United States Patent [19]

Miura et al.

[11] Patent Number: 5,259,238

[45] Date of Patent: Nov. 9, 1993

[54] FLOW TESTER FOR THERMOPLASTIC, AND STRAND CUTTING METHOD

[75] Inventors: Yasuhiro Miura, Chiba; Mitsumasa Ishino, Tokyo, both of Japan

[73] Assignees: Sumitomo Chemical Company, Limited, Osaka; Sumitomo Chemical Engineering Co., Ltd., Tokyo, both of Japan

[21] Appl. No.: 799,544

[22] Filed: Nov. 27, 1991

[30] Foreign Application Priority Data

Nov. 27, 1990 [JP] Japan ................. 2-323723
Jan. 17, 1991 [JP] Japan ................. 3-3771
Jan. 17, 1991 [JP] Japan ................. 3-3774

[51] Int. Cl.$^5$ ............................. G01N 11/04
[52] U.S. Cl. ............................. 73/54.11
[58] Field of Search ............. 73/54.11; 422/63, 64

[56] References Cited

U.S. PATENT DOCUMENTS

| | | | |
|---|---|---|---|
| 2,780,096 | 2/1957 | Noble et al. | 73/54.13 |
| 4,229,970 | 10/1980 | Barker et al. | 73/54.11 |
| 4,449,395 | 5/1984 | Kurtz et al. | 73/54.11 |
| 4,587,837 | 5/1986 | Newbould | 73/54.11 |
| 4,882,930 | 11/1989 | Nagy et al. | 73/54.11 |

FOREIGN PATENT DOCUMENTS

| | | |
|---|---|---|
| 0014025 | 8/1980 | European Pat. Off. . |
| 278683 | 8/1988 | European Pat. Off. . |
| 577578 | 6/1933 | Fed. Rep. of Germany ..... 73/54.11 |
| 275196 | 1/1990 | Fed. Rep. of Germany . |
| 3900664 | 7/1990 | Fed. Rep. of Germany . |
| 285061 | 12/1990 | Fed. Rep. of Germany . |
| 52-051990 | 4/1977 | Japan . |
| 61-043533 | 3/1986 | Japan . |
| 81545 | 4/1987 | Japan ................. 73/54.11 |
| 9004184 | 4/1990 | PCT Int'l Appl. . |
| 9100992 | 1/1991 | PCT Int'l Appl. ........ 73/54.11 |

*Primary Examiner*—Tom Noland
*Assistant Examiner*—Joseph W. Roskos
*Attorney, Agent, or Firm*—Birch, Stewart, Kolasch & Birch

[57] ABSTRACT

According to the present invention, there is provided a flow tester for thermoplastic which uses an extrusion type plastometer including a vertically supported cylinder, a piston on which a weight is mounted at an upper portion thereof and which is inserted in the cylinder, a die mounted on a lower end of the cylinder, and a heater provided to surround the cylinder, characterized in that a sample of a thermoplastic is filled in the cylinder and is heated by the heater to melt, the molten sample is extruded from the die by the piston, a strand as an extruded material is cut, and a mass thereof is obtained, thereby testing a flow characteristic of the thermoplastic, characterized by including a strand bottle which has a cutting edge for cutting the strand and which catches the strand cut by the cutting edge, a strand bottle stocker for storing the strand bottle before and after use, a weight measuring unit for measuring a weight of the cut strand together with the strand bottle, a strand cutting unit for moving the strand bottle so that the cutting edge of the strand bottle travels along a lower end face of the die to perform cutting, and a strand bottle convey unit for transferring and conveying the strand bottle among the strand bottle stocker, the weight measuring unit, and the strand cutting unit.

21 Claims, 15 Drawing Sheets

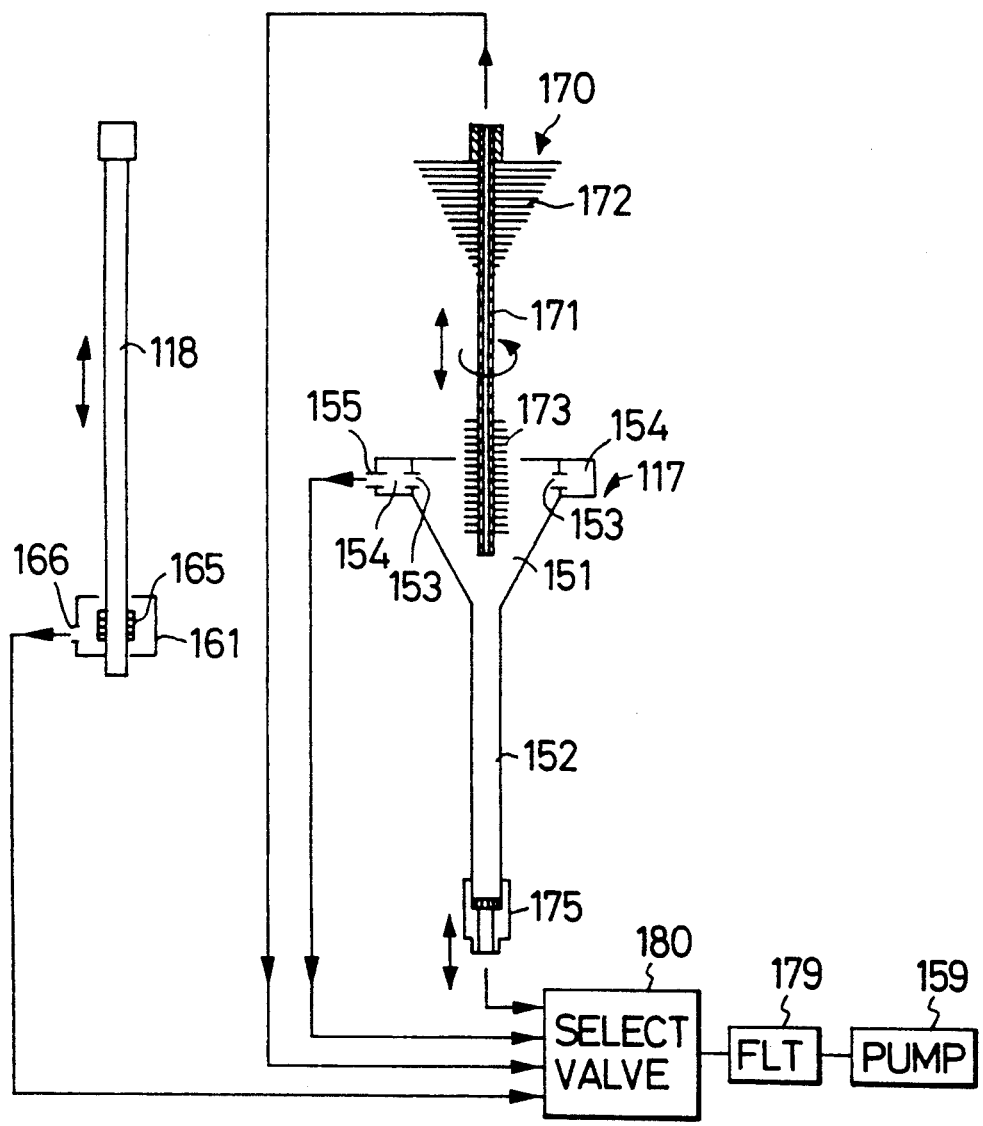

FLOW TESTER FOR THERMOPLASTIC, AND STRAND CUTTING METHOD

BACKGROUND OF THE INVENTION

1. Field of the Invention

The present invention relates to a flow tester for testing a flow characteristic of a thermoplastic and, a strand cutting unit, a plastic sample supply unit, and cleaning unit used by the tester.

1. Related Background Art

A melt-flow characteristic of a polymer material, e.g., a thermoplastic depends on a shear rate and is thus a significant factor as an index in fabrication. Therefore, the melt-flow characteristic is standardized in JIS as "Method of Testing Flow Characteristic of Thermoplastic", JIS K 7210.

This method of testing the flow characteristic uses an extrusion type plastomer comprising a vertically supported cylinder, a piston on which a weight is mounted at an upper portion thereof and which is inserted in the cylinder, a die mounted on a lower end of the cylinder, and a heater provided to surround the cylinder. A sample of a thermoplastic is filled in the cylinder and heated by the heater to melt. Then, the molten sample is extruded from the die by the piston. A mass of the strand as the extruded material per unit time is obtained, converted to a mass extruded per 10 minutes, and determined as an MFR value.

Methods A and B are defined as methods of obtaining the mass of the strand per unit time. According to method A, a strand flowing per unit time is cut, and its mass is weighed. According to method B, a time during which a strand of a unit volume flows out is measured to calculate the mass of the strand. In either method, the test described above is repeated three times, and their average is obtained and determined as the MFR value.

In this manner, according to the method A, a strand extruded from the die is cut (sheared) three times. Conventionally, in order to cut the strand, a person who conducts the test uses a spatulate cutting member and performs cutting by sliding the cutting member along the lower end face of the die.

In the cutting operation, a strand having a high viscosity must be cut instantaneously at a predetermined timing. Therefore, in a conventional manual operation by a testing person, an individual difference occurs, or a difference between maximum and minimum values of the measurement values becomes large, making it difficult to perform an accurate measurement. In addition, the testing person needs high skill.

A tester of this type described above has a plastic sample supply unit for supplying various types of plastic samples to the plastometer prior to a test.

FIG. 1 schematically shows a conventional plastic sample supply unit. As shown in FIG. 1, this plastic sample supply unit has a sample bottle stocker 202, a bottle tilting means 203, a conveying means 204, a vibrating feeder 205, and a hopper 207. The sample bottle stocker 202 stores a multiple of sample bottles 201. The bottle tilting means 203 tilts the sample bottles 201. The conveying means 204 transfers and conveys the sample bottles 201 between the sample bottle stocker 202 and the bottle tilting means 203. The vibrating feeder 205 receives a sample Sa which pours out from the sample bottle 201 by the bottle tilting means 203. The hopper 207 receives the sample Sa supplied from the vibrating feeder 205 and guides it to a cylinder 206a of a plastometer 206. Various types of samples Sa are stored in the sample bottles 201 in advance. Each sample Sa is taken out from the sample bottle stocker 202 and transferred to the bottle tilting means 203 by the conveying means 204. The sample Sa transferred to the bottle tilting means 203 pours out onto the vibrating feeder 205 from the sample bottle 201 and is guided to the down stream hopper 207 by vibration of the vibrating feeder 205. The sample Sa guided to the hopper 207 is collected by a taper portion 207a of the hopper 207 and is filled in the cylinder 206a of the plastometer 206 through a tube 207b continuous with the taper portion 207a. Then, the sample Sa filled in the cylinder 206a is sufficiently rammed by a rammer 208 to prevent bubbles from being generated in the sample Sa.

In this manner, in a conventional plastic sample supply unit, when an adherent sample or a powder type sample is to be handled, the sample Sa can easily adhere to the inner circumferential surface of the sample bottle 201. Even when the sample bottle 201 is tilted, the sample Sa sometimes does not completely pour out and remains in the sample bottle 201. Since the tube 207b portion of the hopper 207 is arcuated, the sample Sa can clog in the arcuated portion to cause a so-called bridge, and the sample Sa may not be completely supplied to the plastometer 206.

In addition, the sample remaining on the inner surface of the hopper is mixed in a sample of a subsequent test to denature it. Therefore, conventionally, a continuous automatic operation of the tester is stopped, and the operator manually cleans the hopper and the rammer.

Such a cleaning operation is cumbersome and takes longer time than an actual test does, thus prolonging the entire operation time required for the test. Also, during the cleaning operation, the residual sample is scattered in the air to contaminate the periphery of the tester.

SUMMARY OF THE INVENTION

The present invention has been made in view of the above situation, and to achieve its objects described below.

1. To provide a flow tester for a thermoplastic, that can perform accurate cutting and measurement of a strand, and a strand cutting method by the tester.

2. To provide a flow tester for a thermoplastic, that has a plastic sample supply unit which can smoothly and reliably supply a plastic sample to a plastometer.

3. To provide a flow tester for a thermoplastic, that has a cleaning unit and a hopper which enable automatic removal of a residual sample.

It is one object of the present invention to provide a flow tester for a thermoplastic which uses an extrusion type plastometer comprising a vertically supported cylinder, a piston on which a weight is mounted at an upper portion thereof and which is inserted in the cylinder, a die mounted on a lower end of the cylinder, and a heater provided to surround the cylinder, wherein a sample of a thermoplastic is filled in the cylinder and is heated by the heater to melt, the molten sample is extruded from the die by the piston, a strand as an extruded material is cut, and a mass thereof is obtained, thereby testing a flow characteristic of the thermoplastic, characterized by a strand bottle which has a cutting edge for cutting the strand and which catches the strand cut by the cutting edge, a strand bottle stocker for storing the strand bottle before and after use, a weight measuring unit for measuring a weight of the cut strand together with the strand bottle, a strand cutting unit for moving the strand bottle so that the cutting edge of the strand bottle travels along a lower end face of the die to perform cutting, and a strand bottle convey unit for transferring and conveying the strand bottle among the strand bottle stocker, the weight measuring unit, and the strand cutting unit.

In the above invention, first, the strand bottle is conveyed from the strand bottle stocker to the weight measuring unit to measure the weight of the empty strand bottle. Then, the strand bottle is conveyed from the weight measuring unit by the strand bottle convey unit to the strand cutting unit and is set to it. Before preparing the strand cutting unit, a pellet or powder type plastic sample is filled in the extrusion type plastometer and is heated to melt. A flow test conforming to the method A of JIS K 7210 is started.

That is, the strand cutting unit is moved toward the strand, extruded from the plastometer at a predetermined timing, and the strand is cut with the cutting edge of the strand bottle set to the strand cutting unit. The cut strand drops in or is caught in the strand bottle while it adheres to the cutting edge.

When cutting of the strand is completed, the strand bottle convey unit is driven again to convey the strand bottle from the strand cutting unit to the weight measuring unit. The weight measuring unit measures the weight of the strand bottle containing the strand. The results of the first and second weight measurements are subjected to subtraction to obtain the weight of the strand itself. After that, the mass of the strand is obtained in accordance with the JIS calculation equation. Finally, the strand bottle is conveyed to the strand bottle stocker and is stored at a predetermined position.

If the strand bottle convey unit has a convey robot and the reference positions of the respective units are stored in the robot, the strand bottle can be automatically conveyed.

It is one object of the present invention, to provide a flow tester for a thermoplastic providing a strand cutting unit, the flow tester using an extrusion type plastometer comprising a vertically supported cylinder, a piston on which a weight is mounted at an upper portion thereof and which is inserted in the cylinder, a die mounted on a lower end of the cylinder, and a heater provided to surround the cylinder, wherein a sample of a thermoplastic is filled in the cylinder and is heated by the heater to melt, the molten sample is extruded from the die by the piston, a strand as an extruded material is cut, and a mass thereof is obtained, thereby testing a flow characteristic of the thermoplastic, characterized in the strand cutting unit comprising a strand bottle which has a cutting edge for cutting the strand and which catches the strand cut by the cutting edge, fixing means for placing and fixing the strand bottle on a base, elevating means for vertically moving the strand bottle through the fixing means so as to move the cutting edge of the strand bottle between an abutting position to abut against a lower end face of the die and a separate position as a position before and after a cutting operation, and reciprocating means for reciprocating the strand bottle through the fixing means so as to cause the cutting edge to travel between a cutting start position and a cutting end position by sandwiching the die in between.

In this case, first, the fixed strand bottle is moved upward by the elevating means through the fixing means until the cutting edge of the strand bottle abuts against the lower end face of the die of the plastometer. Then, the strand bottle is quickly moved forward by the reciprocating means toward the extruded strand at a predetermined timing so that the cutting edge cuts the strand. The strand bottle is designed to catch the strand cut by the cutting edge. Thus, the strand is cut and automatically stored in the strand bottle.

If the fixing means is constituted to be capable of detaching the strand bottle from the base, the weight of the strand can be measured in units of strand bottles without removing it from the strand bottle, and the strand can be stored in units of strand bottles.

If the fixing means is constituted by the first fixing means for guiding insertion of the strand bottle and fixing the travel direction and the second fixing means for fixing the vertical direction, when the strand bottle is vertically moved by the elevating means, only the strand bottle can be vertically moved by using the first fixing means as a guide, and the first fixing means can be utilized to receive the action force which occurs during cutting.

In this case, if the first fixing means has a recess and a projection to regulate the movement of the strand bottle in the horizontal rotating direction, the direction of the cutting edge of the strand bottle can be accurately directed in a predetermined direction. If the second fixing means has the chucking port for chucking the strand bottle, the strand bottle can be fixed and released easily for setting and detaching. If the chucking port is constituted by an elastic member, the chucking operation can be performed easily, and the cutting edge is biased toward the die together with the strand bottle so that it will not separate from the lower end face of the die even during travel.

It is a further object of the present invention to provide a flow tester for thermoplastic, providing a strand cutting unit, characterized in that the strand cutting unit is capable of loading three strand bottles thereon, and the strand cutting unit further comprises control means for controlling cutting travel of the strand bottles at desired time intervals.

According to the above invention, the strand bottle is caused to travel for cutting by the control means at time intervals conforming to the JIS, and three strand bottles can catch the strand. With this series of cutting and catching operations, three test operations required by the JIS are completed without any loss. In this case, if the control means has a control section to stop and move the strand bottle downward immediately after cutting, the cutting edge separates from the lower end face of the die quickly, and the cut strand will not partly adhere to the die or remain on its lower end face.

If the base has the cutting mechanism for cutting the preheated strand and the strand is cut by the cutting mechanism after a lapse of a predetermined period of preheating time, the test start (start of sample acquisition) is automatically set by this cutting.

In this case, if the cutting mechanism has the moving means for moving the cutting edge between the cutting position and the escape position, during test cutting, the cutting edge can escape from the die so as not to interfere with the test cutting. If the cutting edge is mounted through one point to be capable of being inclined in the direction of the edge trace with respect to the moving means, the entire edge trace direction of the cutting edge is inclined along the lower end face of the die, thereby maintaining the abutting state against the die during cutting. If the cutting mechanism is a strand bottle having the cutting edge, the preheated strand (strand for waste cutting) can be stored in the strand bottle.

It is a further object of the present invention to provide a flow tester for a thermoplastic providing a strand bottle, the flow tester using an extrusion type plastometer comprising a vertically supported cylinder, a piston on which a weight is mounted at an upper portion thereof and which is inserted in the cylinder, a die mounted on a lower end of the cylinder, and a heater provided to surround the cylinder, wherein a sample of a thermoplastic is filled in the cylinder and is heated by the heater to melt, the molten sample is extruded from the die by the piston, a strand as an extruded material is cut, and a mass thereof is obtained, thereby testing a flow characteristic of the thermoplastic, characterized in the strand bottle comprising a bottle body for catching the cut strand, and a cutting edge for strand cutting, the cutting edge being fixed to the bottle body while a tip thereof is located immediately above a bottle mouth of the bottle body.

According to the above invention, the cutting edge is fixed to the bottle body while its tip is located immediately above the bottle mouth. Therefore, the strand cut by the cutting edge automatically drops in the bottle body. Even if the strand adheres to the cutting edge, the strand is not separated from the strand bottle, and can be caught.

In this case, if the edge trace of the cutting edge is substantially perpendicular to the cutting direction, the cutting time is shortened, and the strand having a high viscosity can be effectively cut. Since the cutting edge is formed as a V-shape edge, the strand after cutting will not easily adhere to the cutting edge.

If the bottle body is formed as a polygonal prism, the cutting edge can be easily mounted on it and the bottle body can be easily held by a robot or the like during conveyance. If the bottle mouth of the bottle body is set to be larger than the distance of the cutting movement, the strand (measurement sample) before cutting which is extruded from the die can be kept in the bottle body until cutting.

It is a further object of the present invention to provide a strand cutting method of a flow tester for a thermoplastic, the flow tester using an extrusion type plastometer comprising a vertically supported cylinder, a piston on which a weight is mounted at an upper portion thereof and which is inserted in the cylinder, a die mounted on a lower end of the cylinder, and a heater provided to surround the cylinder, wherein a sample of a thermoplastic is filled in the cylinder and is heated by the heater to melt, the molten sample is extruded from the die by the piston, a strand as an extruded material is cut, and a mass thereof is obtained, thereby testing a flow characteristic of the thermoplastic, characterized by a strand bottle comprising a cutting edge for strand cutting and a bottle body for catching the strand cut by the cutting edge, and moving the strand bottle such that the cutting edge thereof travels along a lower end face of the die, thereby cutting the strand.

In the strand cutting method, it is preferable that three strand bottles are used, and cutting of the strand by these strand bottles is sequentially performed at desired time intervals.

According to the above invention, since the cutting edge is fixed to the bottle body, when the strand is cut by the cutting edge, the cut strand automatically drops in the bottle body. Alternatively, even if the strand adheres to the cutting edge, it is not separated from the strand bottle and can be caught.

If three strand bottles of this type are prepared, three test operations required by the JIS are completed within a short period of time with this cutting and catching operation.

It is a further object of the present invention to provide a flow tester for a thermoplastic providing a plastic sample supply unit, wherein a thermoplastic sample is filled in a cylinder of an extrusion type plastometer, heated to melt, and extruded from a die at a lower end of the cylinder by a piston, thereby testing a flow characteristic of the plastic sample, characterized in the plastic sample supply unit comprising a sample container for containing the plastic sample, tilting means for tilting the sample container until a position where the plastic sample contained therein pours out, rotating means, interlocked with the tilting means, for rotating the sample container, and a hopper for receiving the plastic sample which has poured out and for guiding the plastic sample to the cylinder.

According to the above invention, a sample container is rotated by the rotating means while it is tilted by the tilting means. That is, the sample container is gradually tilted while it is rotated in order to cause the plastic sample to pour out. The position of the plastic sample in the sample container is sequentially shifted along with the rotation, and is separated from the inner circumferential surface of the sample container to pour out into the hopper. The plastic sample which has poured out is guided into the cylinder of the plastometer through the hopper.

In this case, if the agitating means having the agitating member which is capable of reciprocating along the inner circumferential surface of the sample container is provided, even a sample adhering to the inner circumferential surface of the sample container can be scraped by the agitating member and separated from the inner circumferential surface.

In these cases, if the vibrating means for vibrating the hopper is provided, the plastic sample that pours out from the sample container to the cylinder through the hopper does not easily cause a bridge while it passes through the hopper.

Furthermore, in these cases, if the hopper has the taper portion and the straight pipe portion, the plastic sample that passes through the hopper is not easily decelerated, and the plastic sample is smoothly guided into the cylinder. Because of the straight portion, even if a bridge occurs, it can be easily eliminated by a rammer or the like. In addition, if the sample cannot be entirely filled in the cylinder, the excessive sample can be temporarily stored in the straight pipe portion, allowed to melt, and extruded into the cylinder as required.

It is a further object of the present invention to provide a flow tester for a thermoplastic providing a cleaning unit, wherein, prior to a flow test of a thermoplastic that a thermoplastic sample is filled in a cylinder of an extrusion type plastometer, heated to melt, and extruded from a die at a lower end of the cylinder by a piston, thereby testing a flow characteristic of the plastic sample, the cleaning unit cleans a sample supply hopper for guiding the plastic sample to the cylinder, and a rammer, in order to remove a residual sample of a precedent test, characterized in the cleaning unit comprising brush means, inserted in the hopper, for scraping the residual sample adhering to an inner surface of the hopper, hopper suction cleaning means, connected to one end of the hopper, for drawing by vacuum the residual sample scraped by the brush means, scraping means, which has a contact member in which the rammer is inserted, and which slidably moves the rammer in an axial direction relative to the contact member, thereby scraping the residual sample adhering to the rammer, and rammer suction cleaning means which stores the contact member in a case and which draws by vacuum the residual sample scraped off into the case by the contact member.

According to the above invention, after the residual sample adhering to the inner surface of the hopper is scraped by the brush means, it is subjected to suction processing by the hopper suction cleaning means connected to one end of the hopper. The residual sample adhering to the surface of the rammer is scraped off into the case by a slidable contact movement of the rammer relative to the contact member of the scraping means, and is subjected to suction processing by the rammer suction cleaning means.

In this manner, the residual sample adhering to the inner surface of the hopper or the surface of the rammer that directly contacts the sample is automatically removed, and the removed sample is drawn by vacuum without scattering in air.

In this case, if the brush means has the rod and the brush body comprising the first brush matching the shape of the inner surface of the taper portion and the second brush matching the shape of the inner surface of the straight pipe portion, the brush can completely reach the entire inner surface of the hopper, and cleaning that matches the shape of the inner surface of the hopper is enabled. In addition, if the brush means has the motor for rotating the brush body and the actuator for inserting and removing the brush body in and from the hopper, the brush can more completely reach the entire inner surface of the hopper because of the rotational movement and the inserting movement of the brush body.

If the hopper suction cleaning means incorporates the rotary brush, the lower end of the hopper which is connected to the cylinder for sample supply and to which a molten sample can easily adhere can be reliably cleaned.

If the scraping means and the rammer suction cleaning means are arranged on the same axis as that of the hopper located at the sample supply position, the slidable movement of the scraping means can also be used as a sample ramming operation by the rammer. In this case, the contact member of the scraping means which is stored in the case of the rammer suction cleaning means can be used as a guide member of the sample ramming operation.

It is a further object of the present invention to provide a flow tester for a thermoplastic providing a sample, supply hopper unit, wherein, prior to a flow test of a thermoplastic that a thermoplastic sample is filled in a cylinder of an extrusion type plastometer, heated to melt, and extruded from a die at a lower end of the cylinder by a piston, thereby testing a flow characteristic of the plastic sample, the hopper unit guides the plastic sample to the cylinder, characterized in the sample supply hopper unit comprising a suction opening formed in an inner circumferential surface at an upper end portion of the hopper, and suction means communicating with the suction opening according to the above invention, since the suction opening formed in an inner circumferential surface of the upper end portion of the hopper and suction means communicating with the suction opening are provided, the residual sample scraped during cleaning is drawn by vacuum without scattering to the outside. In addition, during supply of the powder type sample prior to this cleaning, the sample which is blown out is drawn by vacuum without scattering to the outside.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 16 is a conceptional view of peripheral members of a vacuum pump.

DESCRIPTION OF THE PREFERRED EMBODIMENT

A flow tester for a thermoplastic according to an embodiment of the present invention will be described with reference to FIGS. 2 through 4.

Figure 1:
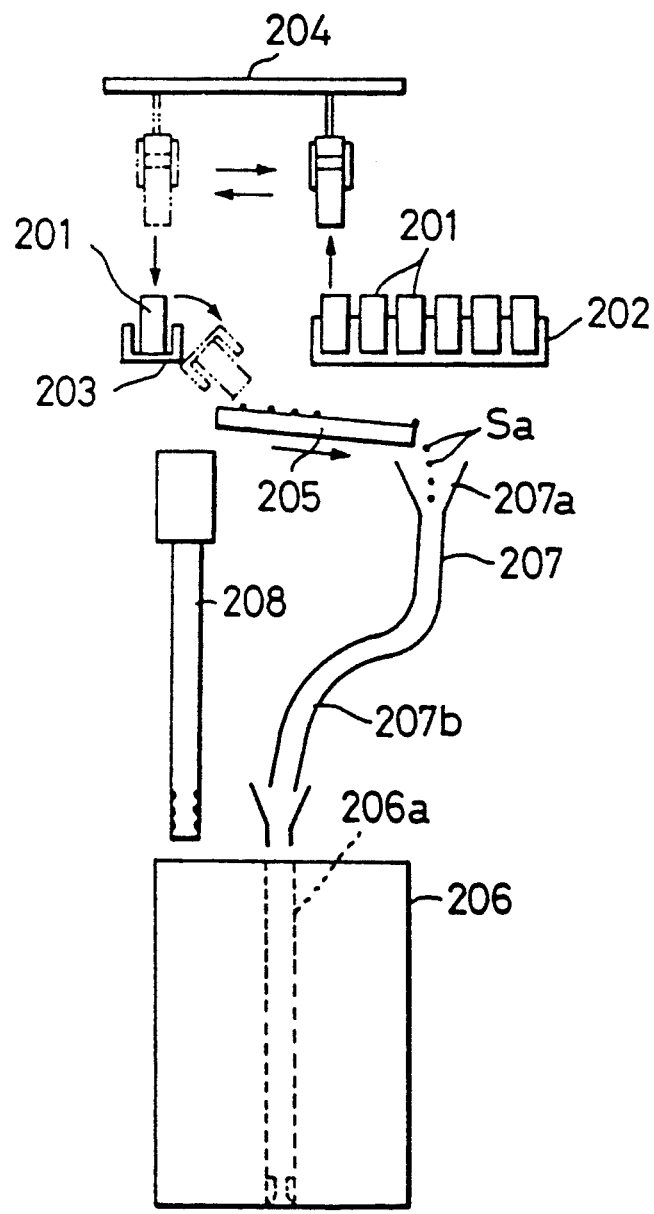
FIG. 1 is a schematic view of a conventional apparatus.
Figure 2:
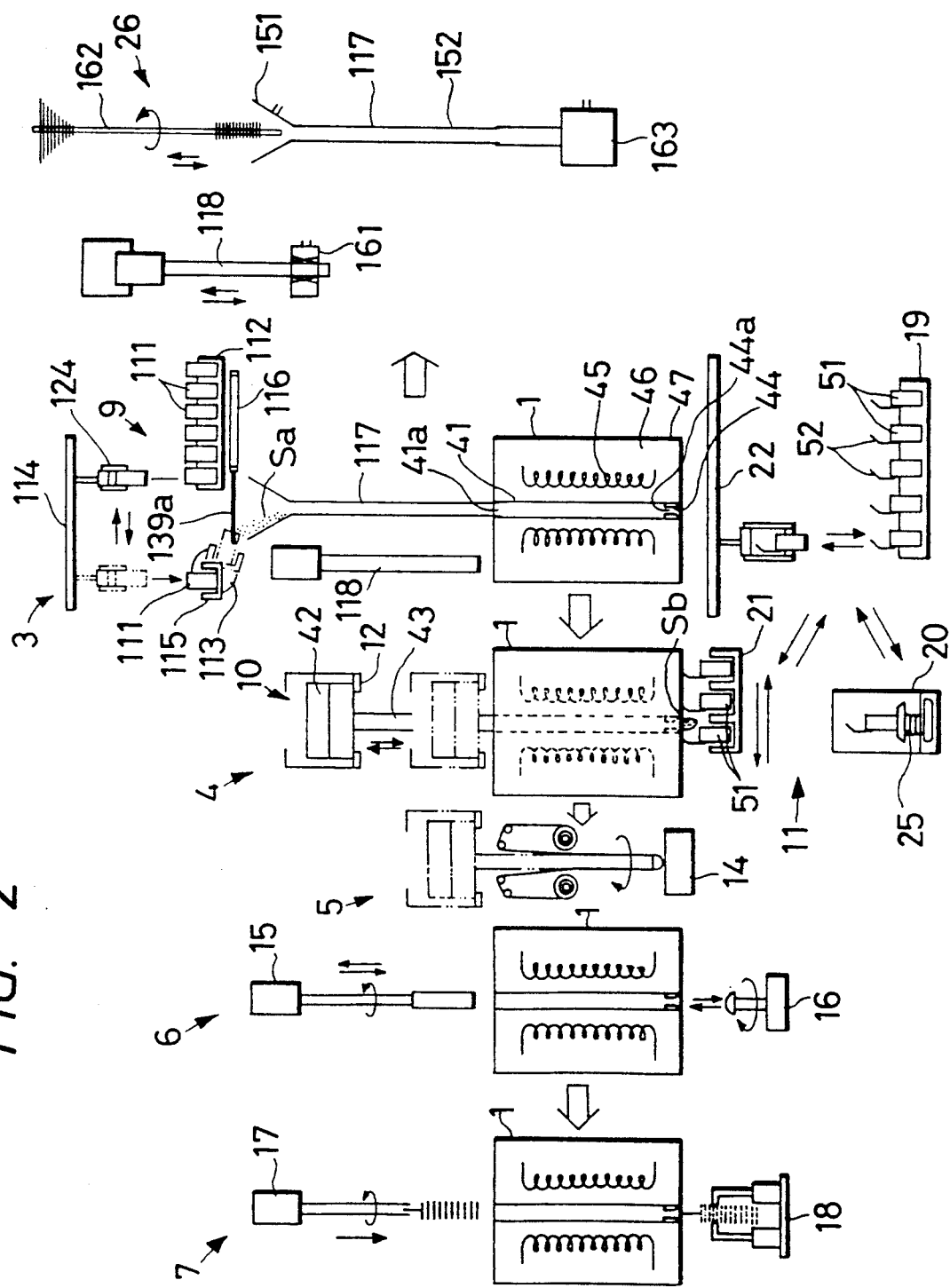
FIG. 2 is a schematic view of an automated apparatus to which a flow tester for thermoplastic according to an embodiment of the present invention is applied.
Figure 3:
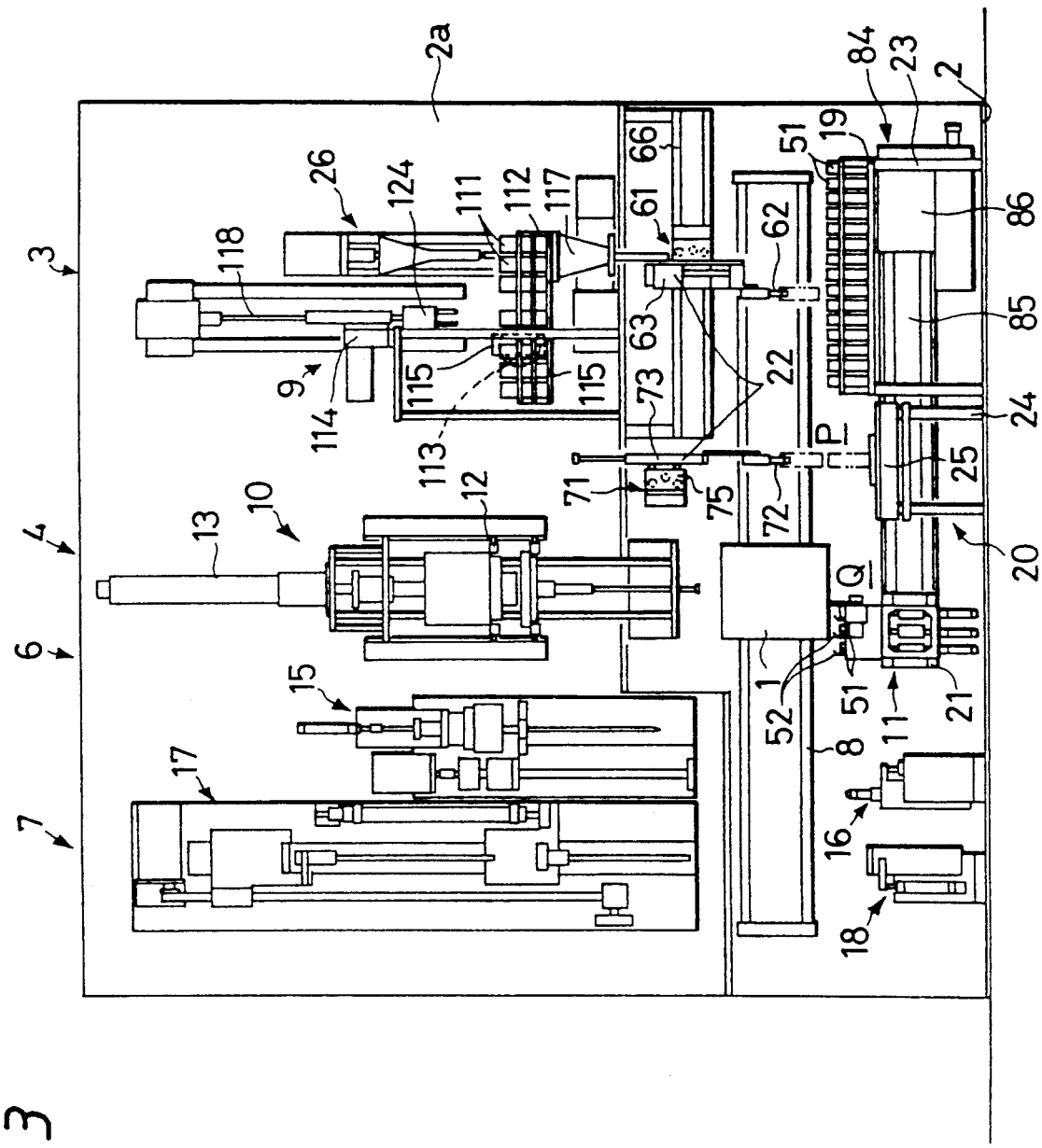
FIG. 3 is a front view of the automated apparatus shown in FIG. 2.
Figure 4:
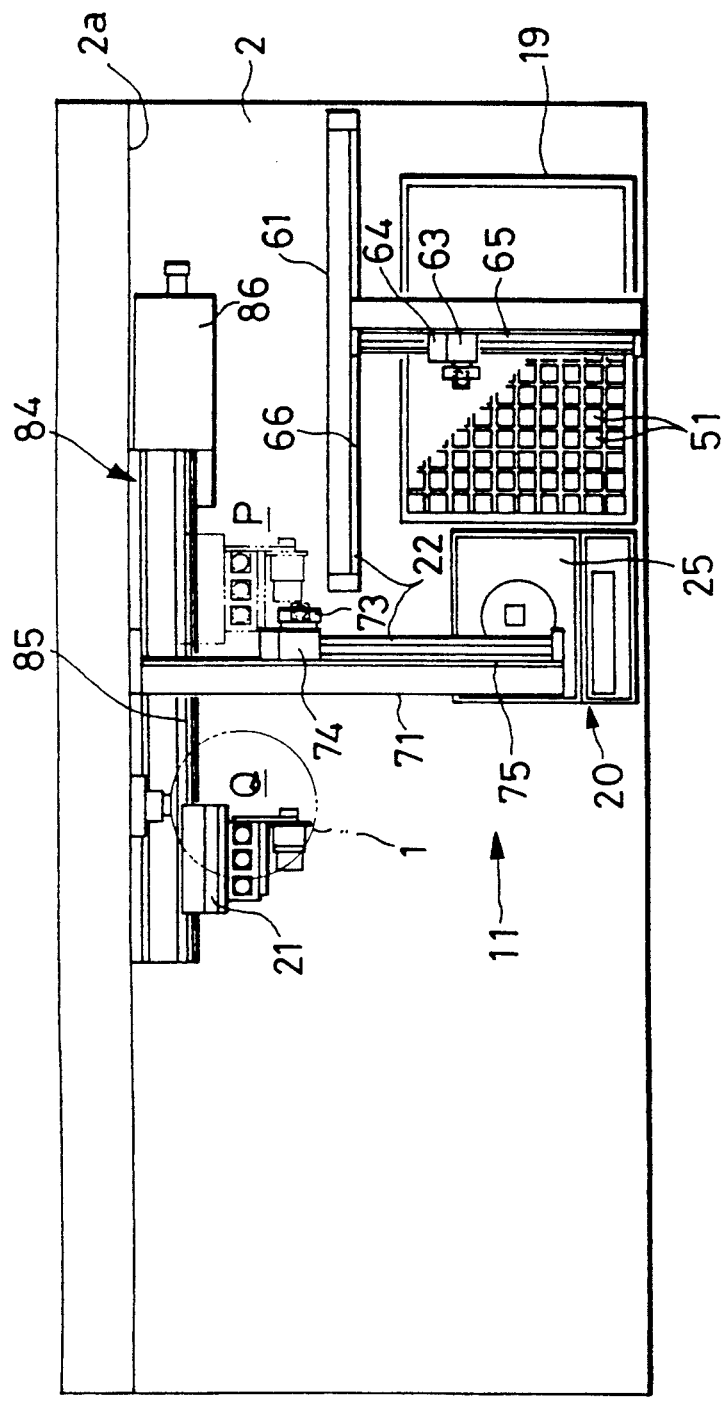
FIG. 4 is a plan view of the automated apparatus in which some constituent equipment is omitted.

FIG. 2 is a schematic view of an automated apparatus of the flow tester for a thermoplastic, FIG. 3 is a front view of the overall structure of the flow tester, and FIG. 4 is a plan view of the overall structure of the flow tester from which some constituent units are omitted.

As shown in FIGS. 2 and 3, in the automated apparatus, an extrusion type plastometer 1 constituting the main body of the flow tester is mounted on a wall surface 2a of a machine table 2 to be movable in the horizontal direction. The plastometer 1 is moved to sequentially oppose a sample supply section 3, a testing section 4, a piston cleaning section 5 (see FIG. 2), a cylinder cleaning section 6, and a die cleaning section 7 of the automated apparatus.

The extrusion type plastometer 1 comprises a vertically supported cylinder 41, a piston 43 on which a weight 42 is mounted at its upper portion and which is inserted in the cylinder 41, a die 44 mounted on a lower end of the cylinder 41, and a heater 45 provided to surround the cylinder 41. The heater 45 is a so-called electric furnace and is surrounded by a heat-insulating material 46 and a case 47 to constitute the columnar plastometer 1 as a whole. Therefore, an upper opening 41a adhere of the cylinder 41 and a lower opening 44a of the die 44 are formed at substantially the central positions of the upper and lower surfaces of the plastometer 1.

The plastometer 1 is movable to the right and left (see FIG. 3) along a movable rail 8 mounted on a lower central portion of the side wall 2a of the machine table 2. Prior to the test, the plastometer 1 opposes the sample supply section 3 as the start point to receive a sample Sa of a thermoplastic. That is, the sample Sa is filled in the cylinder 41 of the plastometer 1 by the plastic sample supply unit 9 arranged in the sample supply section 3. Note that prior to the filling operation of the sample Sa, the cylinder 41 is heated to a predetermined test temperature by the heater 45.

The plastometer 1 filled with the sample Sa is moved along the movable rail 8 to oppose the testing section 4. Then, a test conforming to a method A or B of JIS K 7210 is conducted. That is, according to the method A, the sample Sa heated to the predetermined temperature and molten in the cylinder 41 is extruded through the lower opening 44a of the die 44 by the piston 43 on which the weight 42 of a predetermined weight is mounted. A strand Sb as the extruded material is acquired three times as the measurement sample at predetermined timings within a predetermined range of a downward movement of the piston 44. The respective three strands Sb are weighed, and the obtained values are applied to a calculation equation to obtain an average of the mass.

On the other hand, according to method B, when the sample Sa is to be extruded from the piston 43, on which the weight 42 of the predetermined weight is mounted, through the lower opening 44a of the die 44, a time during which the piston 43 moves a predetermined distance is measured by a timer. This measurement is repeated three times, and the obtained values are applied to a calculation equation to obtain an average of the mass of the sample Sa. In FIGS. 2 and 3, the configuration of the units matching method B is omitted. Therefore, an explanation will be made on the configuration of the units matching method A.

In order to automatically perform the test of method A, a piston drive unit 10 is arranged on the side wall 2a of the machine table 2 in an upper portion of the testing section 4, and a strand processing unit 11 is arranged on the machine table 2 in the lower portion of the testing section 4. The piston drive unit 10 has a retainer 12 and an air cylinder 13. The retainer 12 retains the piston 43 by its weight 42 in a wait position prior to extrusion of the sample Sa by the piston 43. The air cylinder 13 retracts the piston 43 after extrusion of the sample Sa is completed.

In the strand processing unit 11, the strand Sb is automatically cut in accordance with the method A, weighed, and stocked at a predetermined position.

When the test conforming to the JIS (Japan Industries Standard) is completed, the plastometer 1 is moved along the movable rail 8 to sequentially oppose the piston cleaning section 5 (see FIG. 2), the cylinder cleaning section 6, and the die cleaning section 7. In the piston cleaning section 5, the surface of the piston 43 is cleaned by a piston cleaner 14 (see FIG. 2). In the cylinder cleaning section 6, the inner surface of the cylinder 41 and the lower opening 44a of the die 44 are cleaned by a cylinder cleaner 15 and a bottom cleaner 16. In the die cleaning section 7, the inner surface of the die 44 is cleaned by a die cleaner 17 and a cleaning rod remover 18. When the plastometer 1 is cleaned in this manner to completely remove a residual sample Sa from it, it is returned to the initial position opposing the sample supply section 3 along the movable rail 8 to wait for the next sample testing.

The strand processing unit 11 will be described briefly with reference to FIGS. 2 and 4 and in detail with reference to FIGS. 5 to 9.

As shown in FIGS. 2 to 4, the strand processing unit 11 has a strand bottle 51, a strand bottle stocker 29, a weight measuring unit 20, a strand cutting unit 21, and a strand bottle convey unit 22. The strand bottle 51 has a cutting edge 52 for cutting the strand Sb and catches the strand Sb cut by the cutting edge 52. The strand bottle stocker 19 stores the strand bottle 51 before and after use. The weight measuring unit 20 measures the weight of the cut strand Sb. The strand cutting unit 21 moves the strand bottle 51 such that its cutting edge 52 travels along a lower end face 44b of the die 44 of the plastometer 1 to perform cutting. The strand bottle convey unit 22 transfers and conveys the strand bottle 51 among the strand bottle stocker 19, the weight measuring unit 20, and the strand cutting unit 21.

The strand bottle 51 is conveyed from the strand bottle stocker 19 to the weight measuring unit 20 by the strand bottle convey unit 22, and is weighed in an empty state. Then, the strand bottle 51 is conveyed from the weight measuring unit 20 to the strand cutting unit 21 and is set to it. A flow test conforming to the JIS is started. That is, the strand Sb extruded from the plastometer 1 is cut by the cutting edge 52 of the strand bottle 51 which is moved by the strand cutting unit 21 at a predetermined timing. The cut strand Sb drops in the strand bottle 51 or is caught in the strand bottle 51 as it adheres to the cutting edge 52. When cutting of the strand Sb is completed, the strand bottle convey unit 22 is driven again to convey the strand bottle 51 from the strand cutting unit 21 to the weight measuring unit 20. The weight measuring unit 20 weighs the strand bottle 51 as it stores the strand Sb.

Finally, the strand bottle 51 is conveyed to the strand bottle stocker 19 and is stored at a predetermined position.

Figure 5:
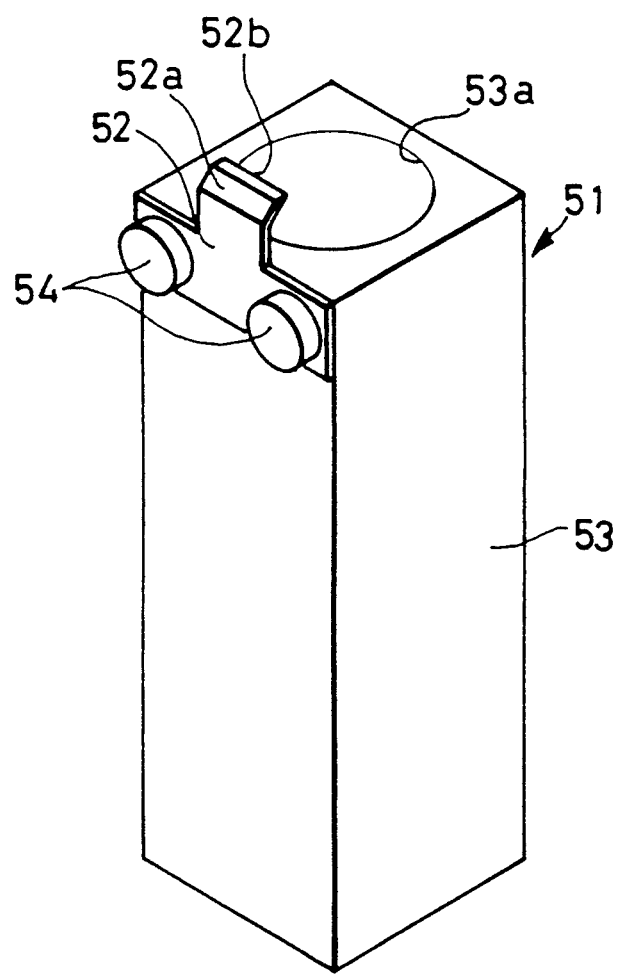
FIG. 5 is a perspective view of a strand bottle used by the tester.

As shown in FIG. 5, the strand bottle 51 comprises a bottomed bottle body 53 and the cutting edge 52. The bottle body 53 is obtained by hollowing out the interior of a quadrangular prism-shaped aluminum die cast in a columnar manner. The cutting edge 52 is clamped to an upper portion of the bottle body 53 by screws 54. The strand Sb cut by the cutting edge 52 can be dropped into the bottle body 53. A tip 52a of the cutting edge 52 is formed as a V-shaped edge to slightly incline inwardly, and the distal end of the tip 52a is located immediately above a bottle mouth 53a of the bottle body 53. The direction of inclination of the tip 52a coincides with the cutting direction of the strand Sb when it is set to the strand cutting unit 21. The upper portion of the tip 52a is ground to form a horizontal surface as the sharp tip 52a. At the same time, the tip 52a can be brought in tight contact with the lower end face 44b of the die 44 of the plastometer 1 with this horizontal surface. An edge trace 52b of the cutting edge 52 is perpendicular to the cutting direction. Therefore, the strand Sb can be cut within a short period of time. In order to prevent the strand from easily adhering to the cutting edge, e.g., liquid paraffin may be effectively sprayed to the cutting edge immediately before cutting the strand. The inner surface of the strand bottle 51 may be effectively coated with a resin to prevent adhesion to the cutting edge.

The diameter of the bottle mouth 53a of the bottle body 53 is formed to be larger than a travel distance (cutting movement) of the strand bottle 51 to be described later. The extruded strand Sb constantly droops in the bottle body 53 even at the cutting movement start position (see FIG. 9).

In this manner, when the strand bottle 51 is set to the strand cutting unit 21 to cut the strand Sb (and when the testing person performs manual cutting as well), the strand Sb after cutting is stored in the bottle body 53. Therefore, if the weight of the strand bottle 51 is measured in advance, the weight of the strand Sb together with the strand bottle 51 can be obtained. In addition, the strand Sb can be caught even when the cutting speed is low and the strand Sb after cutting adheres to the tip 52a of the cutting edge 52. Therefore, the cutting speed need not be set extremely high. In this embodiment, the outer shape of the bottle body 53 is determined as a quadrangular prism shape. However, it can have a polygonal prism shape, e.g., a hexagonal prism or an octagonal prism that can be easily held by a robot arm or the like.

The strand bottle 51 constituted in this manner is transferred and conveyed among the strand bottle stocker 19, the weight measuring unit 20, and the strand cutting unit 21 by the strand bottle convey unit 22.

As shown in FIGS. 3 and 4, the strand bottle convey unit 22 comprises first and second convey systems 61 and 71. The first convey system 61 conveys the strand bottle 51 between the strand bottle stocker 19 and the weight measuring unit 20. The second convey system 71 conveys the strand bottle 51 between the weight measuring unit 20 and the strand cutting unit 21. Each system constitutes a robot controlled by a computer (not shown). The first convey system 61 has a holding arm 62, an air cylinder 63, an air actuator 64, and a Y-axis direction rail 65. The holding arm 62 holds the strand bottle 51. The air cylinder 63 vertically moves the holding arm 62. The air actuator 64 slidably moves the holding arm 62 and the air cylinder 63 in the Y-axis direction. The Y-axis direction rail 65 guides this slidable movement. In addition to the Y-axis direction rail 65, the first convey system 61 also has an actuator (not shown) for slidably moving the holding arm 62 and the air cylinder 63 in the X-axis direction, and an X-axis direction rail 66 for guiding this slidable movement.

The X- and Y-axis direction rails 65 and 66 are arranged in a T-shaped manner. The first convey system 61 is fixed to the machine table 2 through two ends of the Y-axis direction rail 65.

Similarly, the second convey system 71 has a holding arm 72, an air cylinder 73, an air actuator 74, and a Y-axis direction rail 75. The holding arm 72 holds the strand bottle 51. The air cylinder 73 vertically moves the holding arm 72. The air actuator 74 slidably moves the holding arm 72 and the air cylinder 73 in the Y-axis direction. The Y-axis direction rail 75 guides this slidable movement. The second convey system 71 is fixed to the machine table 2 through one end of the Y-axis direction rail 75 in a cantilevered manner.

A plurality of strand bottles 51 are arranged on a placing table 23 of the strand bottle stocker 19 in a matrix. The strand bottles 51 can be supplied as required in order to conduct consecutive tests of multiple of types of samples Sa. The weight measuring unit 20 is constituted by placing an electronic balance 25 on a holding table 24. The weight measuring unit 20 is adjusted such that, when an empty strand bottle 51 is weighed and consecutively a strand bottle containing a strand Sb is weighed, only the weight of the strand Sb is obtained by subtraction and displayed. It is naturally possible to connect the electronic balance 25 to a personal computer in order to arithmetically compute the mass of the strand Sb.

Conveyance and transfer of the strand bottle 51 will be described in due order.

First, the air actuator 64 of the first convey system 61 is driven to move its holding arm 62 to a position immediately above a strand bottle 51 at a designated position. Then, the air cylinder 63 is driven to move the holding arm 62 downward to a holding position of the strand bottle 51. At this time, the holding arm 62 is driven to hold the strand bottle 51 and move it upward to a convey position. Subsequently, the strand bottle 51 is slidably moved along the X- and Y-axis direction rails 65 and 66 while it is held by the holding arm 62, and is conveyed to a position immediately above a central portion of the electronic balance 25. The holding arm 62 is moved downward by the air cylinder 63, and the strand bottle 51 is transferred onto the electronic balance 25. The weight of the strand bottle 51 is measured by the electronic balance 25 simultaneously when it is transferred, and is stored in the electronic balance 25.

When this weight measurement is completed, the air actuator 74 of the second convey system 71 is driven. That is, in the same manner as the above operation, the strand bottle 51 on the electronic balance 25 is held and conveyed to a bottle transfer position P of the strand cutting unit 21 and is set to the strand cutting unit 21. The series of above operations is repeated three times, and three strand bottles 51 are set to the strand cutting unit 21.

When the test is completed, the strand cutting unit 21 is moved to the bottle transfer position P with the strand bottles 51 containing the cut strands Sb set to it. In response to this, the strand bottle convey unit 22 conveys the strand bottles 51 to the strand bottle stocker 19 in accordance with an order reverse to that described above in order to stock them. That is, first, the second convey system 71 is driven to convey the strand bottle 51 to the electronic balance 25 so as to measure the weight of the strand Sb. Then, the first convey system 61 is driven to convey the strand bottle 51 to the strand bottle stocker 19. This operation is repeated three times, and a test for a single sample is completed by this series of operations.

In this manner, the strand bottle stocker 19, the electronic balance 25, and the strand cutting unit 21 are arranged at necessary positions, and the strand bottles 51 are transferred and conveyed among them by the strand bottle convey unit 22 as required.

Therefore, an operation starting from supply of the strand bottle 51 and terminated with stock of the cut strand Sb can be automatically performed.

Figure 6:
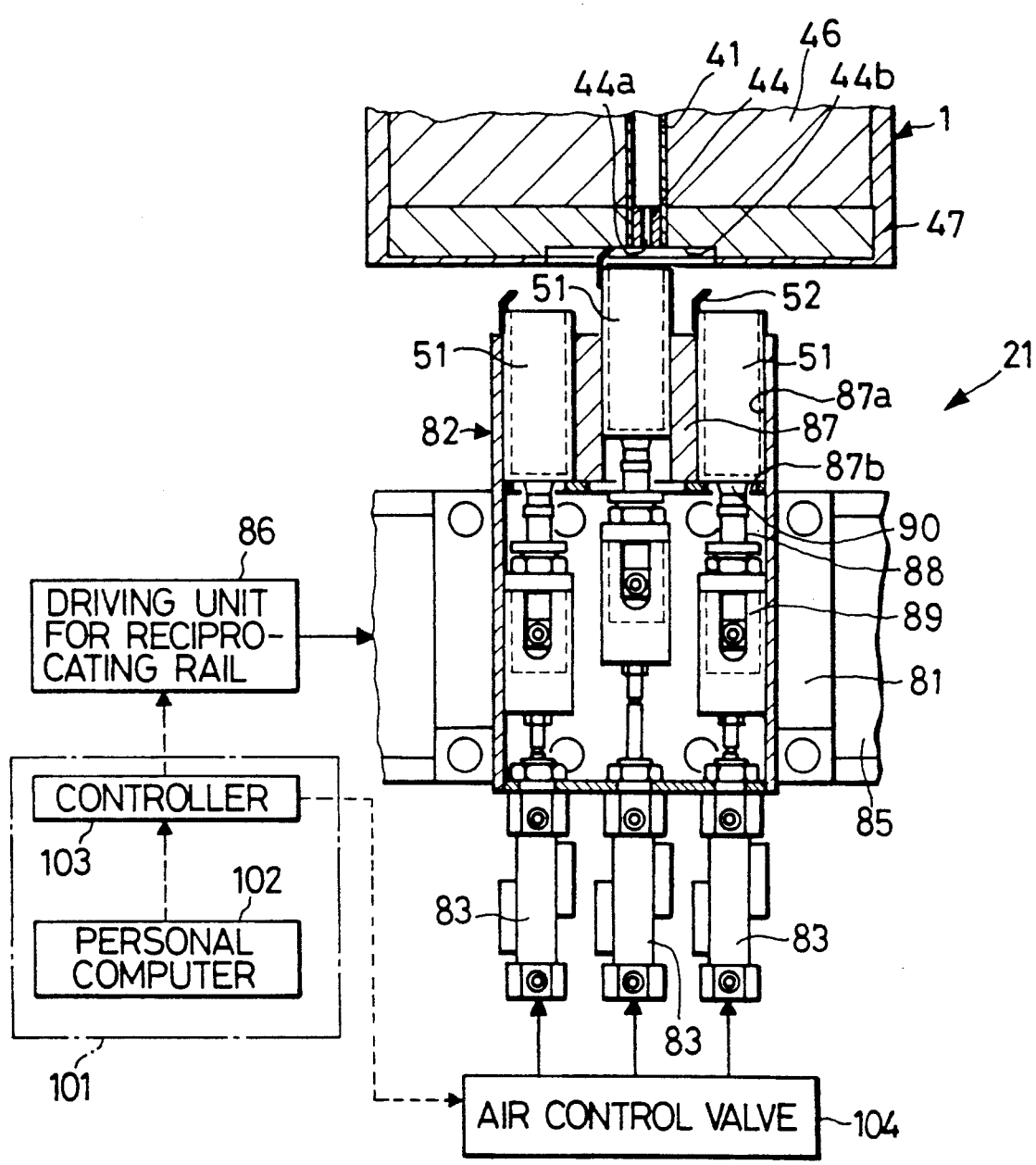
FIG. 6 is a partially cutaway front view of a strand cutting unit applied to the tester.

The strand cutting unit 22 will be described with reference to FIGS. 6 to 8. FIG. 6 is a sectional front view of the strand cutting unit 22, FIG. 7 is a side view of the same, and FIG. 8 is a plan view of the same.

Figure 7:
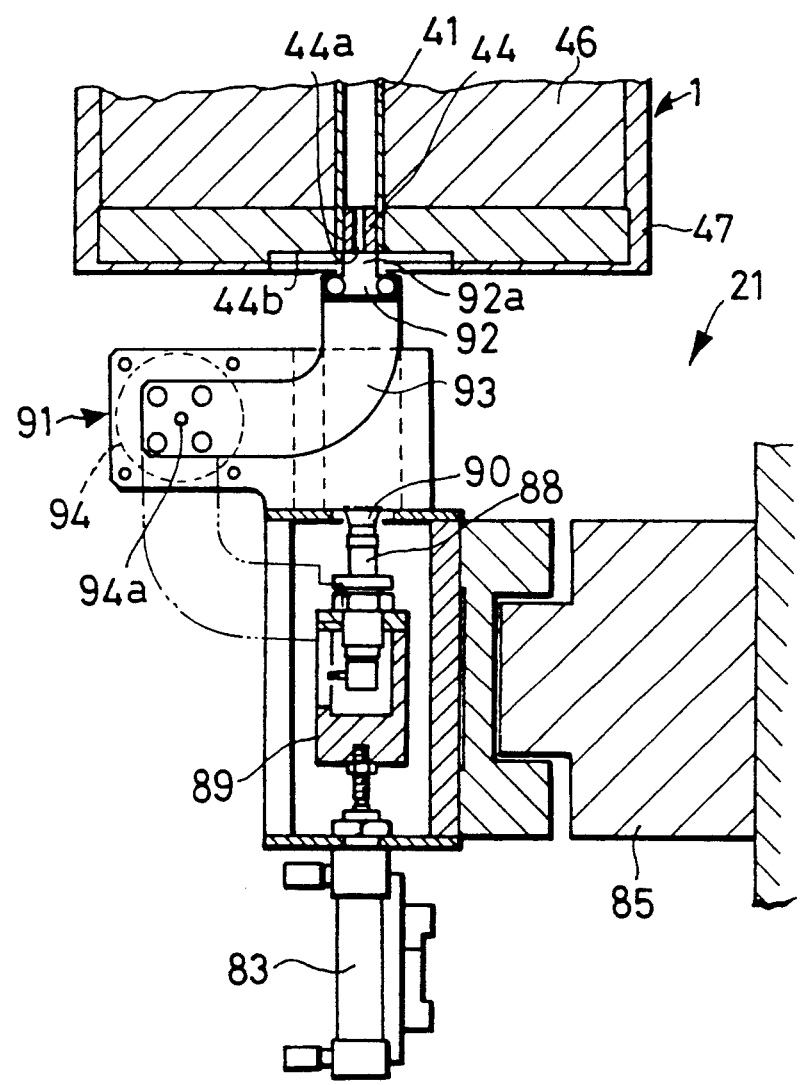
FIG. 7 is a side view of the strand cutting unit.
Figure 8:
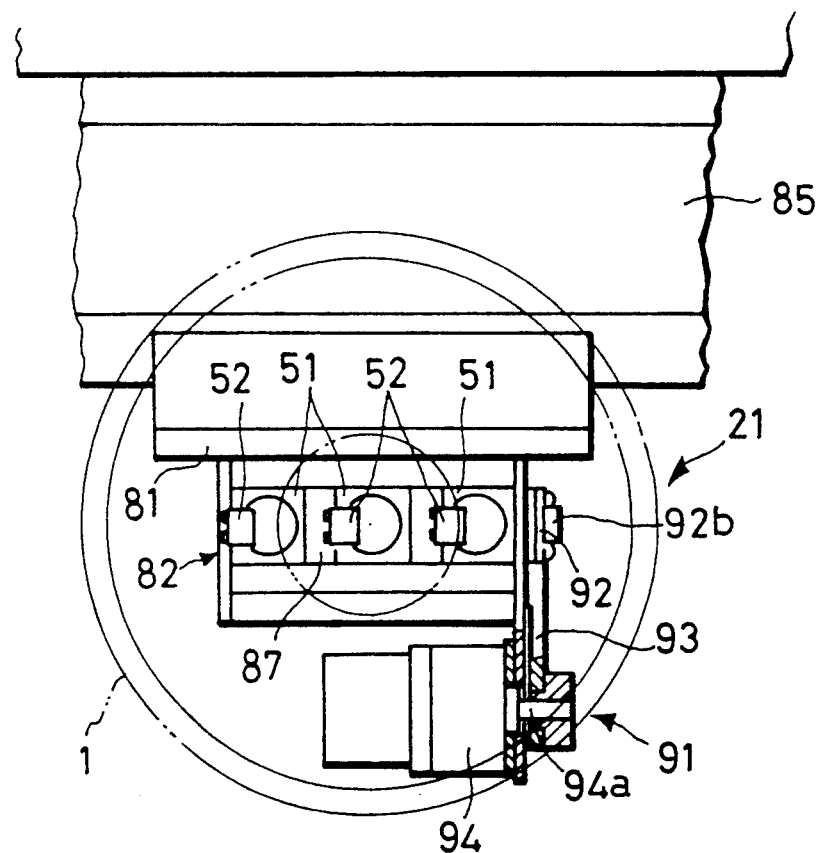
FIG. 8 is a plan view of the strand cutting unit.

As shown in FIGS. 6 to 8, the strand cutting unit 22 has a base 81, three strand bottles 51, fixing means 82, three elevating cylinders 83, and a reciprocating rail 84. The fixing means 82 places the strand bottles 51 on the base 81 and fixes them on it. The elevating cylinders 83 elevate the strand bottles 51 through the fixing means 82. The reciprocating rail 84 (see FIG. 4) reciprocates the strand bottles 51 through the fixing means 82. The strand bottles 51 are fixed to the fixing means 82, and the fixing means 82 and the elevating cylinders 83 are mounted on the base 81. The base 81 is movably mounted on the reciprocating rail 84.

The reciprocating rail 84 has a rail section 85 and a drive section 86, as shown in FIGS. 2 and 3. The rail section 85 is mounted on a lower portion of the wall surface 2a of the machine table 2 and extends in the horizontal direction. The drive section 86 reciprocates each strand bottle 51 together with the corresponding elevating cylinder 83 and so on by using the rail section 85 as a guide. A ball screw (not shown) is provided in the rail section 85, and a drive motor (not shown) for rotating the ball screw is incorporated in the drive section 86. Each strand bottle 51 is moved between a test position Q and the strand bottle transfer position P along the reciprocating rail 84 together with the corresponding elevating cylinder and so on. At each of the test position Q and the transfer position P, control is performed so that the three strand bottles 51 are slightly moved to sequentially oppose a predetermined position.

The fixing means 82 has a block member 87 and chucking members 88. Set grooves 87a in which the corresponding strand bottles 51 are inserted are formed in the block member 87. The chucking members 88 oppose the lower surfaces of the corresponding strand bottles 51 through bottom openings 87b of the block member 87 and chuck the strand bottles 51 by vacuum. Each set groove 87a of the block member 87 has a quadrangular prism shape substantially the same as that of the strand bottle 51. Each strand bottle 51 is inserted and set in the corresponding set groove 87a while the tip 52a of its cutting edge 52 is aligned with the cutting direction. Each set groove 87a serves as a guide during vertical movement of the corresponding strand bottle 51 (to be described later), and its inner wall functions to accept the reaction force of the corresponding strand bottle 51 during cutting. Each chucking member 88 comprises a main body 89 and a chucking port 90 communicating with each other through an air ejector (this ejector and a hose are not shown). Each chucking port 90 is made of an elastic material, e.g., a rubber. Therefore, the strand bottle 51 can be easily fixed by chucking. The cutting edge 52 of the strand bottle 51 is abutted against the lower end face 44b of the die 44 of the plastometer 1 while it is slightly biased, thus assuring a cutting operation.

The elevating cylinders 83 are fixed to the lower ends of the chucking members 88, and the strand bottles 51 are vertically moved by the elevating cylinders 83 as required through the chucking members 88. By this vertical movement, the cutting edge 52 of the strand bottle 51 is moved between an abutting position to abut against the lower end face 44b of the die 44 and a separate position as a position before and after the cutting operation. Also, by this vertical movement, the strand bottle 51 is easily transferred to the holding arm 72 of the second convey system 71. This vertical movement is performed for each strand bottle 51.

Although omitted in FIG. 6, a (waste cutting) cutting mechanism 91 for cutting a preheated strand Sb portion which marks the start of test is provided to the front end of the base 81, as shown in FIGS. 7 and 8. The cutting mechanism 91 has a cutting edge 92, an arcuated arm 93, and a pivot cylinder 94. The cutting edge 92 is mounted on the distal end of the arcuated arm 93. The pivot cylinder 94 pivots the arcuated arm 93. The cutting mechanism 91 is fixed to the base 81 through the pivot cylinder 94. The cutting edge 92 has a tip 92a of the same shape as that of the cutting edge 52 of the strand bottle 51. When cutting the strand Sb, the cutting edge 92 is aligned in the same direction as the cutting edge 52 of the strand bottle 51. The base portion of the arcuated arm 93 is fixed to a drive shaft 94a of the pivot cylinder 94. The pivot cylinder 94 pivots, through the arcuated arm 93, the cutting edge 92 between a cutting position for cutting the strand Sb and an escape position to where the cutting edge 92 escapes, as required. At the cutting position, the cutting edge 92 abuts against the lower end face 44b of the die 44 of the plastometer 1 and is driven by the reciprocating rail 84 so that it is moved, together with the base 81, to slide on the lower end face 44b of the die 44, thereby cutting the strand Sb. After cutting the strand Sb, the cutting edge 92 is immediately returned to the escape position so as not to interfere with test cutting. Although the cutting edge 92 is fixed to the distal end of the arcuated arm 93 through two portions, it can be mounted through one position so that it can be inclined in the direction of an edge trace 92b. Then, since the cutting edge 92 is inclined in the direction of the edge trace 92b as required, its contact with the lower end face 44b of the die 44 can be constantly maintained.

It is possible to replace the cutting mechanism 91 with the strand bottle 51. That is, four strand bottles 51 may be set to the strand cutting unit 21, and waste cutting may be performed by the first strand bottle 51. In this case, although the capacity of the strand bottle 51 need be considered, an unnecessary strand Sb which is subjected to waste cutting can be disposed of without being left in the unit.

In this manner, in the strand cutting unit 21, a total of four cutting edges 52 and 92 consisting of the cutting edge 92 for cutting the preheated strand Sb portion and the three cutting edges 52 each for cutting the strand Sb as a test sample are aligned in the cutting direction as required. Therefore, a cutting operation is performed by driving the reciprocating rail 84 to move the cutting edge 92 of the cutting mechanism 91 and the three cutting edges 52 of the strand bottles 51 such that they sequentially abut against the lower end face 44b of the die 44. More specifically, when each cutting edge 52 abuts against the lower end face 44b of the die 44, this state corresponds to an abutting position (cutting position of the cutting mechanism 91) of the elevating cylinder 83, and simultaneously a cutting start position of the reciprocating rail 84. When cutting is completed and the cutting edge 52 is stopped, this position corresponds to a cutting end position of the reciprocating rail 84.

When the cutting edge 52 is moved downward and stopped, this position corresponds to a separate position (escape position of the cutting mechanism 91) of the elevating cylinder 83.

In this manner, each cutting edge 52 or 92 cuts the strand Sb by a series of operations of upward moving, forward moving (travel), and downward moving. These operations are repeated a total of four times to complete the test.

Figure 9:
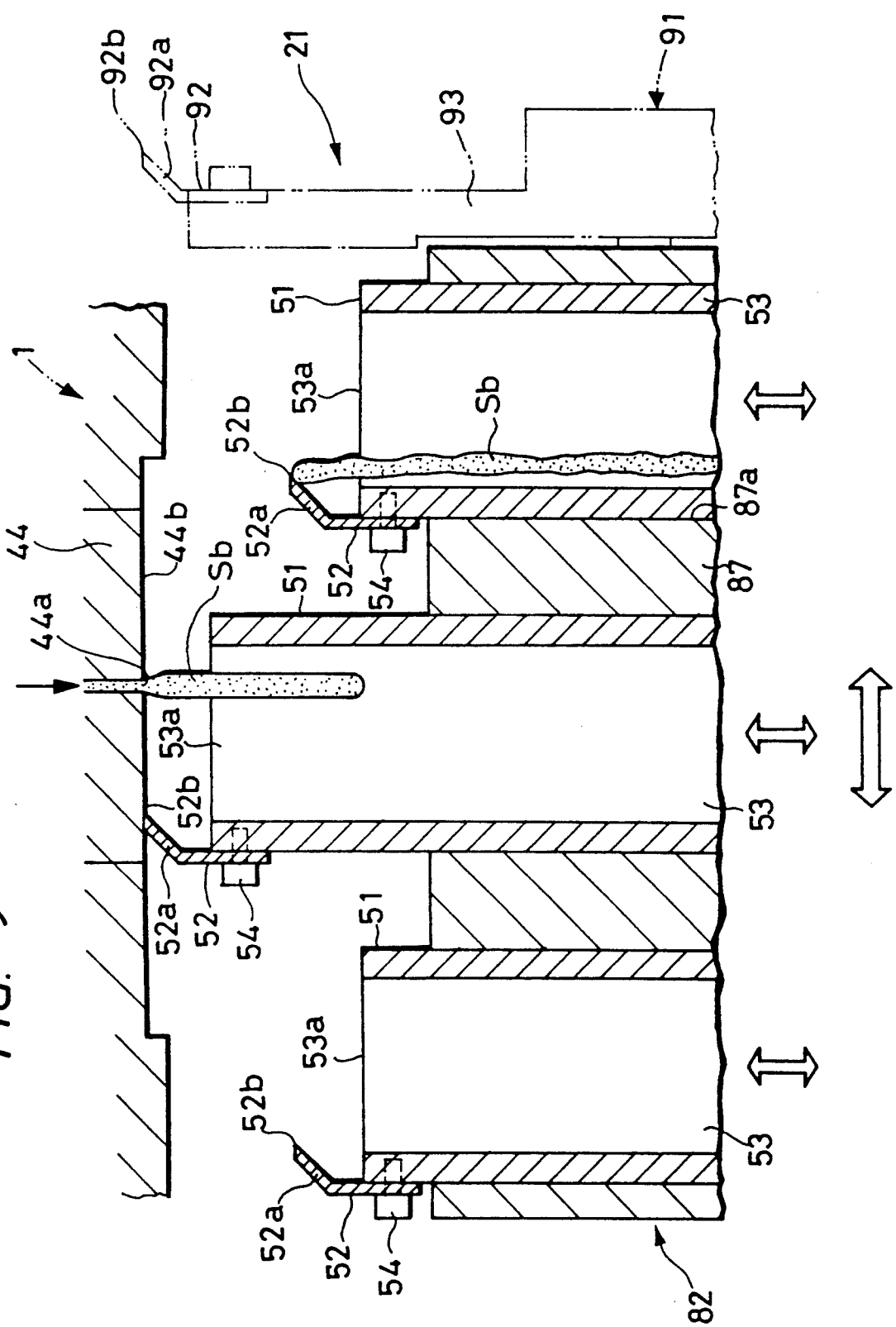
FIG. 9 is a partially enlarged sectional view for explaining the strand cutting state of the strand cutting unit.
Figure 10:
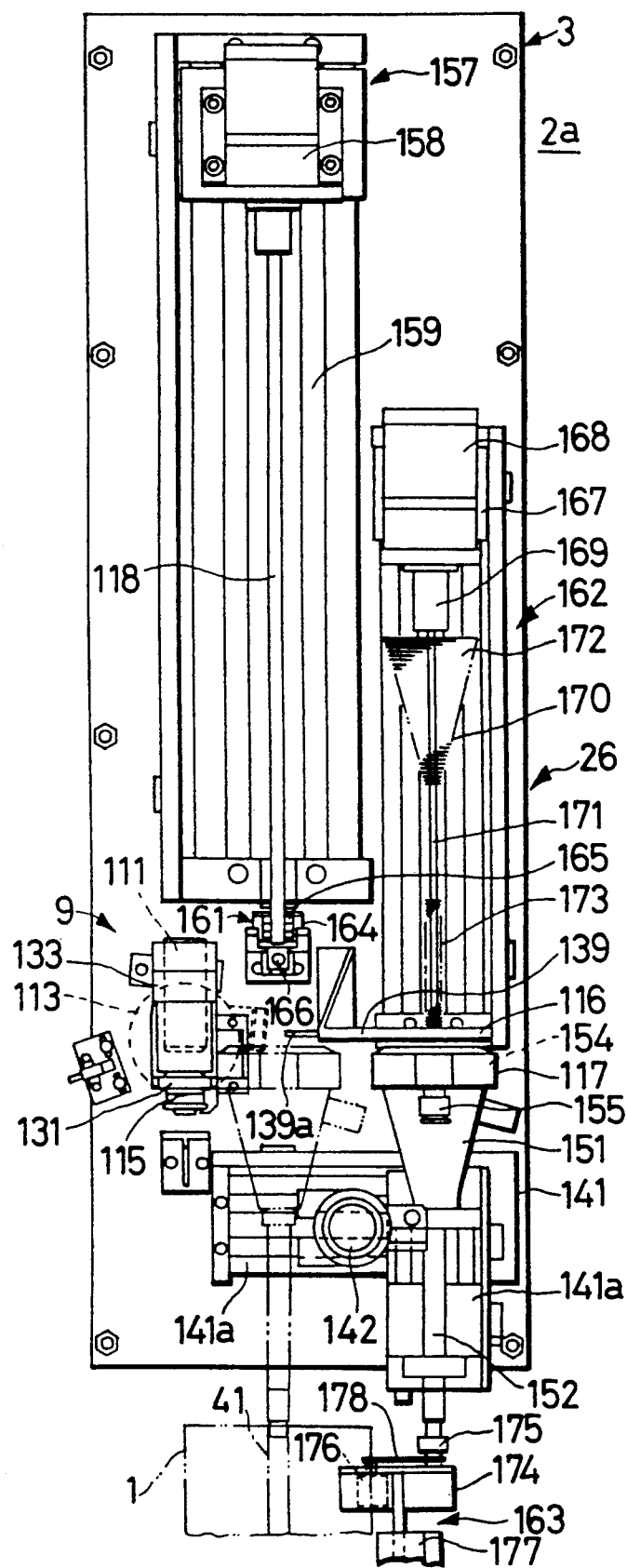
FIG. 10 is a front view of a sample supply section.

The order of cutting the strand Sb will be described with reference to FIG. 9. FIG. 9 shows a state in which the first strand bottle 51 has completed catching the strand Sb and the second strand bottle 51 waits at the cutting start position.

Upon reception of the three strand bottles 51 from the strand bottle convey unit 22, the strand cutting unit 21 is moved to a position immediately under the plastometer 1 by its reciprocating rail 84 (see FIGS. 3 and 4). The test starts in this state. Regarding the strand cutting unit 21, the arcuated arm 93 of its cutting mechanism 91 is pivoted so that its cutting edge 92 is moved to the cutting position, i.e., the cutting start position where it abuts against the lower end face 44b of the die 44 of the plastometer 1, and is set in the wait mode. This state continues until the preheat time has elapsed. Even during preheating, the molten strand Sb is extruded from the die 44. When a predetermined preheat time has elapsed, the reciprocating rail 84 drives to move the cutting edge 92 of the cutting mechanism 91 to cut the strand Sb (waste cutting). When cutting is completed, the cutting edge 92 is immediately automatically moved to the escape position.

This cutting initiates the test, and extrusion and cutting of the strand Sb are repeated a total of three times in accordance with the method A during a predetermined period of time. That is, when the cutting edge 92 of the cutting mechanism 91 is moved to the escape position, simultaneously the base 81 is moved to a predetermined position by the reciprocating rail 84 so that the cutting edge 52 of the first strand bottle 51 reaches a position immediately under the cutting start position. When this movement is completed, the elevating cylinder 83 of the first strand bottle 51 is driven to move the first strand bottle 51 upward until its cutting edge 52 abuts against the lower end face 44b of the die 44, i.e., until the abutting position. Then, the first strand bottle 51 is set in the cutting wait mode. The moving operation so far starting from waste cutting of the preheated strand portion is performed at a rather high speed. When the strand bottle 51 is set in the cutting wait mode, since the bottle mouth 53a of the strand bottle 51 is larger than the cutting movement distance, the strand Sb to be caught is gradually extruded into the strand bottle 51. When a predetermined extrusion time according to the method A is reached, the reciprocating rail 84 is driven to cause the cutting edge 52 of the first strand bottle 51 to travel while it abuts against the lower end face 44b of the die 44, thereby cutting the strand Sb. After being cut, if the strand Sb has a low viscosity, it drops in the strand bottle 51 almost simultaneously with cutting and is caught in it, and if the strand Sb has a high viscosity, it is caught in the strand bottle 51 while adhering to the cutting edge 52. When cutting is completed, the movement of the strand bottle 51 is stopped, and subsequently the strand bottle 51 is moved downward by the elevating cylinder 83 to the separate position.

In this case, the cutting edge 52 is moved in the cutting direction by the reciprocating rail 84 at a high speed. When the cutting edge 52 cuts the strand Sb, simultaneously it is stopped and is moved downward quickly by the elevating cylinder 83, thereby completing the cutting operation. This operation is repeated a total of three times as described above. This operation is controlled by a control means 101 shown in FIG. 6. That is, when the piston 43 is moved downward to reach a measurement start point (when the lower end of the piston 43 reaches a position 50 mm above the upper end of the die 44), this fact is detected by a sensor (not shown), and a personal computer 102 detects a measurement start upon reception of a sensor output, thereby starting drive control. Along with the measurement start, the personal computer 102 sends control signals to the drive section 86 of the reciprocating rail 84 and an air control valve 104 of the elevating cylinders 83 through a control section 103 to start drive as required. A command of "waste cutting" as the "measurement start" is output, and the strand Sb is subjected to waste cutting by the cutting mechanism 91. Then, the first, second, and third cutting commands are output at time intervals stored in the personal computer 102. The strand Sb that has flowed from the die 44 between waste cutting and the first cutting is caught in the first strand bottle 51. The strand Sb that has flowed from the die 44 between the first and second cutting is caught in the second strand bottle 51. The strand Sb that has flowed from the die 44 between the second and third cutting is caught in the third strand bottle 51.

When control is performed in this manner, the strand Sb after cutting can be quickly separated from the lower end face 44b of the die 44, thereby preventing the strand Sb after cutting, especially the strand Sb having a high viscosity from adhering to the die 44.

After the first strand bottle 51 is moved downward, the second strand bottle 51 is moved forward to be located immediately under the die 44. Subsequently, completely the same operation as that for the first strand bottle 51 is performed for the second strand bottle 51. This series of operations are repeated for the third strand bottle 51 as well.

FIG. 9 shows a state in which the second strand bottle 51 is located at the cutting start position (abutting position). In this case, the first strand bottle 51 has completed catching the strand Sb, and the strand Sb to be subjected to a subsequent cutting droops in the second strand bottle 51.

As has been described above, according to this embodiment, the strand bottles 51 having the cutting edges 52 are used and are caused to travel to perform cutting, thereby automatically cutting and catching the strand Sb simultaneously and reliably.

The arrangement of the sample supply section 3 will be described with reference to FIGS. 10 to 13.

At the sample supply section 3, the sample supply unit 9 and a cleaning unit 26 are arranged on the sidewall 2a of the machine table 2. The plastic sample Sa is filled in the cylinder 41 of the plastometer 1 by the sample supply unit 9. A hopper 117 and a rammer 118 (to be described later) that contact the sample Sa directly during supply of the sample Sa are cleaned by the cleaning unit 26.

The sample supply unit 9 has sample bottles 111, a sample bottle stocker 112, a sample bottle tilter 113, a sample bottle conveyor 114, a sample bottle rotator 115, an agitator 116, the hopper 117, and the rammer 118.

The sample bottles 111 are sample containers for storing the sample. The sample bottle stocker 112 stores a multiple of sample bottles 111. The sample bottle tilter 113 is a tilting means for the sample bottles 111. The sample bottle conveyor 114 transfers and conveys the sample bottles 111 between the sample bottle stocker 112 and the sample bottle tilter 113. The sample bottle rotator 115 is a rotating means interlocked with the sample bottle tilter 113 to rotate the sample bottles 111. The agitator 116 is an agitating means for agitating the sample Sa in the sample bottle 111 which is rotated in an inclined state. The hopper 117 guides the sample Sa received from the sample bottles 111 to the cylinder 41. The rammer 118 rams the sample Sa filled in the cylinder 41. The plastic sample Sa is of a pellet or powder type. Various types of samples Sa having adhesion or moisture-absorption properties are subjected to testing. For this purpose, each sample bottle 111 is constituted by a bottomed plastic cylinder, and a lid 111a is prepared so that a sample having moisture-absorption properties can be stored in the sample bottle 111.

Figure 11:
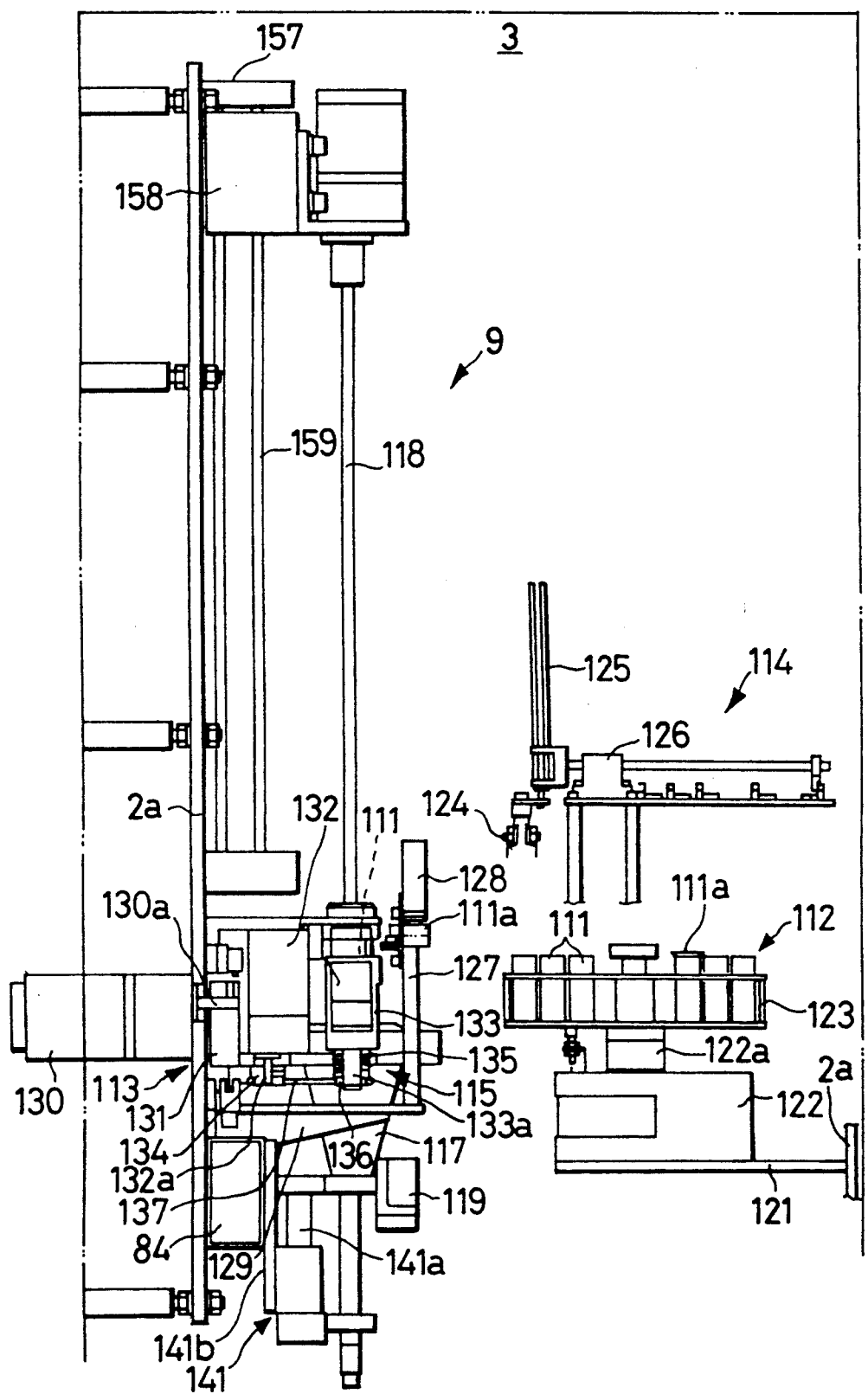
FIG. 11 is a left side view of the sample supply section.
Figure 12:
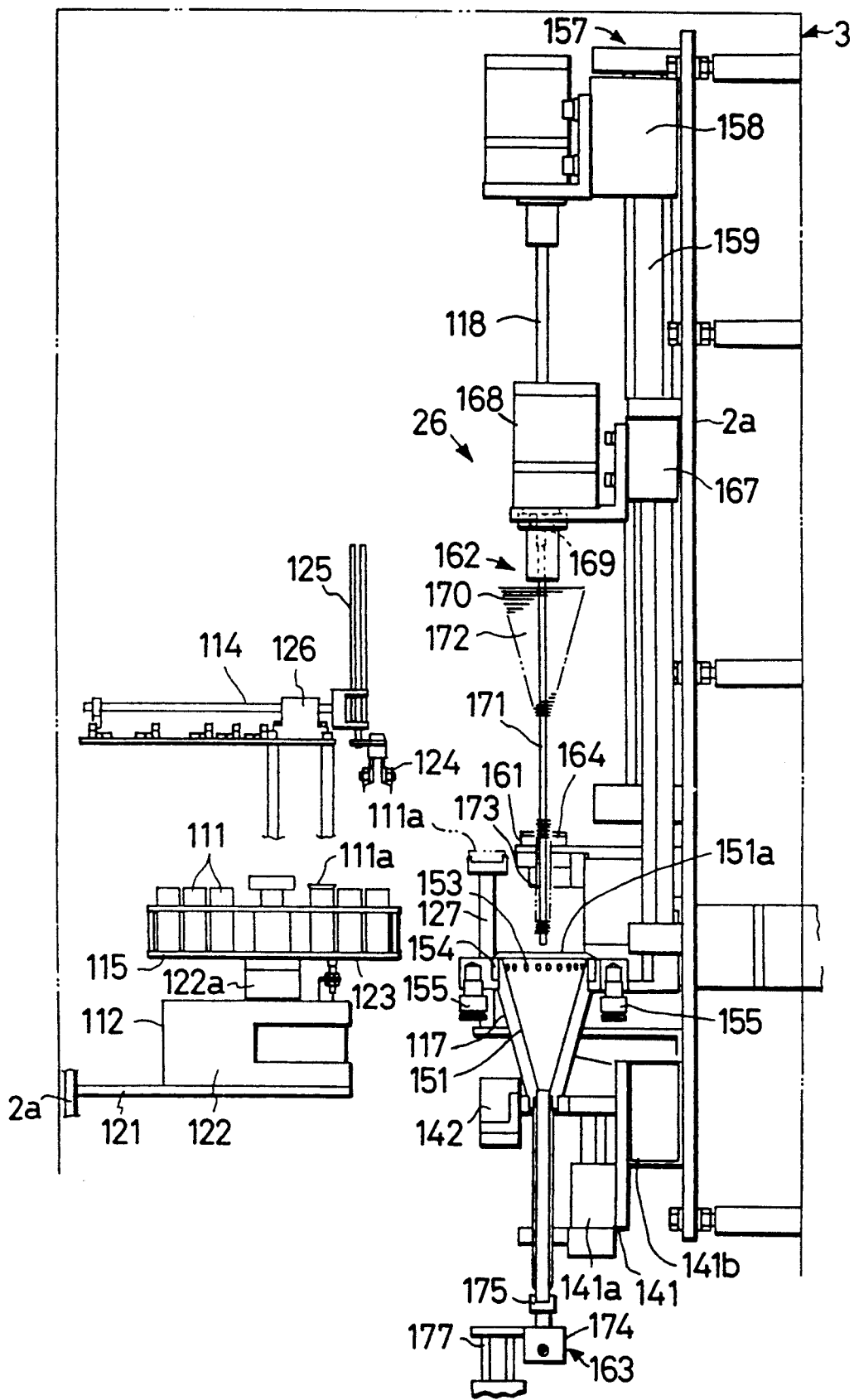
FIG. 12 is a right side view of the sample supply section.

The sample bottle stocker 112 is fixed on a bracket 61 extending from the machine table 2, as shown in FIGS. 11 and 12, and is constituted by a main body 122, a drive motor (not shown), a vertical rotating shaft 122a of the drive motor, and a disc-shaped rotary table 123. The drive motor is incorporated in the main body 122. The rotary table 123 is fixed to the vertical rotating shaft 122a. A multiple of (44 in this embodiment) sample bottles 111 can be set on an upper surface of the rotary table 123. When driven by the rotating drive shaft 122a of the drive motor, the rotary table 123 moves a desired sample bottle 111 to a position opposing the sample bottle conveyor 114.

The sample bottle conveyor 114 is fixed above the bracket 121 described above, and has a holding arm 124 for holding the sample bottles 111, an elevating cylinder 125 for vertically moving the holding arm 124, and a reciprocating actuator 126 for reciprocating the holding arm 124 and the elevating cylinder 125 with respect to the sample bottle tilter 113. When driven by the elevating cylinder 125, the holding arm 124 is moved downward to a position of the sample bottle 111, holds the sample bottle 111 or the lid 111a, and is moved upward.

Subsequently, the reciprocating actuator 126 is driven to move the sample bottle 111 or the lid 111a toward the sample bottle tilter 113. Midway along the trace of the reciprocal movement, a lid rest 127 and a sample bottle detecting sensor 128 are mounted on a bracket 129 extending from the side wall 2a of the machine table 2 to detect whether the holding arm 124 holds the sample bottle 111 or the lid 111a. When the lid 111a is detected, the holding arm 124 and the reciprocating actuator 126 are controlled to transfer the lid 111a to the lid rest 127 and then to convey the sample bottle 111. When the sample bottle 111 is detected, the holding arm 124 and the reciprocating actuator 126 are controlled to transfer the sample bottle 111 directly to the sample bottle tilter 113. When supply of the sample Sa is completed, the sample bottle 111 or the lid 111a is collected in an order reverse to that described above.

The sample bottle tilter 113 is fixed to one side of the side wall 2a of the machine table 2, as shown in FIGS. 3 and 4. A tilt motor 130 is arranged on the rear side of the sample bottle tilter 113 through the sidewall 2a, and an L-shaped tilt bracket 131 is arranged on the front side of the sample bottle tilter 113. The base of the tilt bracket 131 is fixed to a main shaft 130a of the tilt motor 130, and the sample bottle rotator 115 is fixed to the distal end of the tilt bracket 131.

When the tilt motor 130 is driven, the sample bottle tilter 113 is rotated together with the tilt bracket 131, and the sample bottle 111 fixed to the sample bottle tilter 113 is tilted to a position where the sample Sa contained in the sample bottle 111 pours out. This tilting operation is controlled in the following manner. That is, it is performed quickly until the sample bottle 111 is set horizontally. After that, it is tilted slowly to a predetermined tilt position. The tilted state is maintained at the tilt position for a predetermined period of time. Then, the sample bottle 111 is returned to the vertical position quickly.

Figure 13:
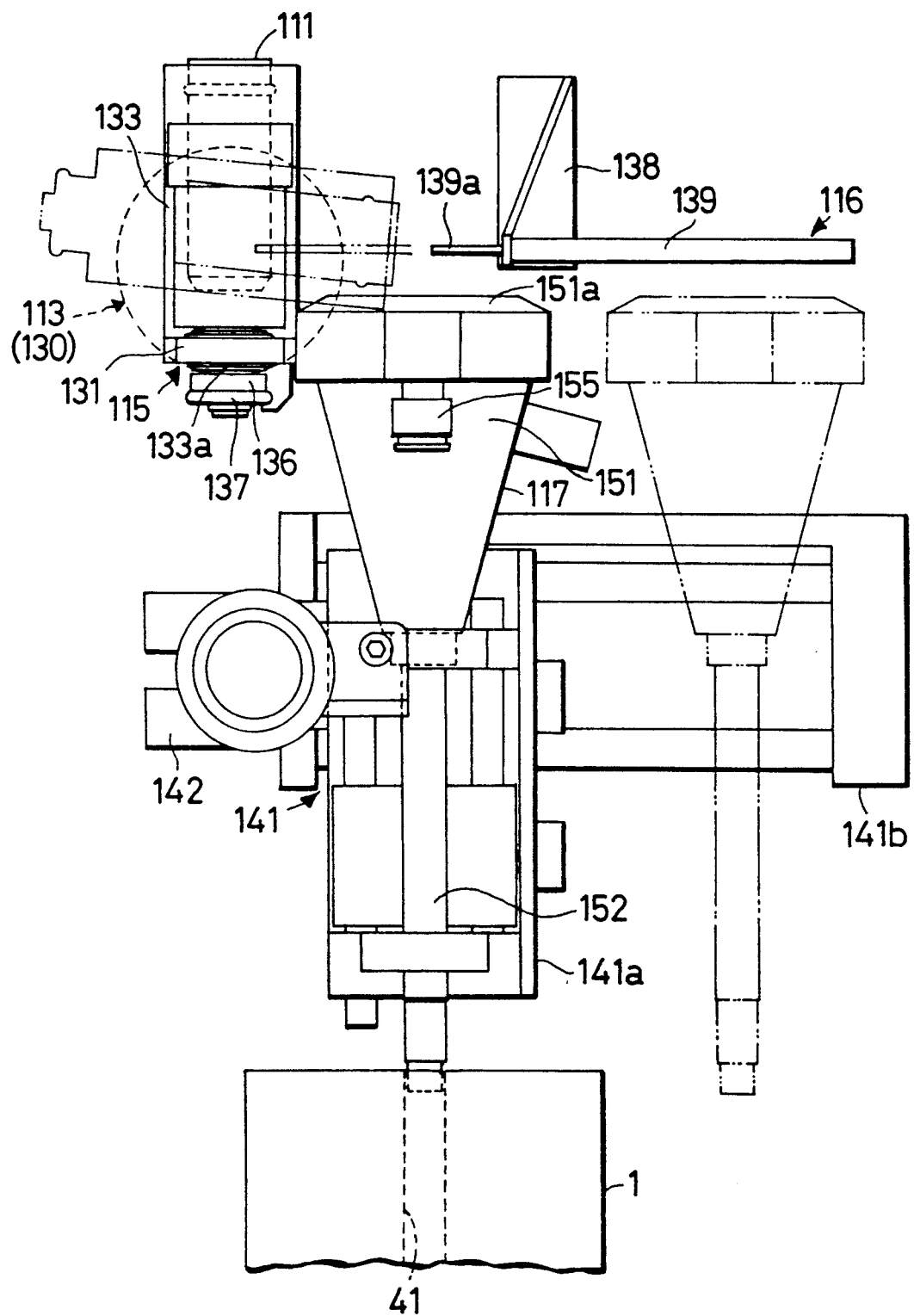
FIG. 13 is a front view of the main part of the sample supply section.

The sample bottle rotator 115 has a rotary motor 133 and a sample bottle holder 134 both fixed to the tilt bracket 131, as shown in FIGS. 11 and 13. A drive pulley 135 is fixed to the distal end of a main shaft 133a of the rotary motor 133 through which the tilt bracket 131 extends. The lower end of the sample bottle holder 134 forms a rotating shaft 134a. The sample bottle holder 134 is rotatably mounted on a bearing 136 which is fixed to the tilt bracket 131 through the rotating shaft 134a. A driven pulley 137 is fixed to the distal end of the rotating shaft 134a, and the rotation of the rotary motor 133 is transmitted to the sample bottle holder 134 through a belt 138 applied between the drive pulley 135 and the driven pulley 137 of the rotary motor 133.

Therefore, the sample bottle holder 134 is rotated by drive of the rotary motor 133, and the sample bottle fixed to the sample bottle holder 134 is rotated about the shaft of the rotary motor 133. This rotation is interlocked with the tilting operation of the sample bottle tilter 113, and the sample bottle 111 is gradually tilted while being rotated. The sample Sa pours out from the sample bottle 111 by this tilting operation. In order to promote outflow of the sample Sa, the agitator 116 opposes the interior of the tilted sample bottle 111.

The agitator 116 is constituted by an air cylinder 139 fixed to the side wall 2a of the machine table 2 through a stationary bracket 138, as shown in FIGS. 11 and 13, and its piston rod 139a serves as an agitating member to oppose the interior of the sample bottle 111. The reciprocal movement of the piston rod 139a is controlled in the following manner. That is, while the sample bottle 111 is moved from the horizontal position to the predetermined tilt position, the piston rod 139a is interlocked with slow pivoting of the sample bottle 111 and moves forward to slide on the inner circumferential surface of the sample bottle 111. When the piston rod 139a reaches a position immediately close to the bottom of the sample bottle 111, it moves backward. Since the sample bottle 111 is tilted while it is rotated, the forward movement of the piston rod 139a serves to agitate the interior of the sample bottle 111. Accordingly, the piston rod 139a is promoted to separate from the inner circumferential surface of the sample bottle 111. The sample Sa which completely pours out drops and is received in the hopper 117 located below the sample bottle 111.

The hopper 117 is mounted on a horizontal/vertical movable rail 141, and the horizontal/vertical movable rail 141 is fixed to the side wall 2a of the machine table 2. The hopper 117 is fixed to a vertical rail 141a of the horizontal/vertical rail 141, and the lower end of hopper 117 is moved between insertion and separate positions where it is inserted in and removed from the plastometer 1. The vertical rail 141a is mounted on a horizontal rail 141b of the horizontal/vertical rail 141 as the hopper 117 is fixed on the vertical rail 141a. Therefore, the hopper 117 is moved between a supply position where the sample Sa is supplied and a cleaning position where the hopper 117 is cleaned.

The hopper 117 is constituted by a taper portion 151 and a straight pipe portion 152. The taper portion 151 receives the pouring sample Sa. The straight pipe portion 152 is continuous with the taper portion 151 and guides the sample Sa to the cylinder 41 of the plastometer 1. For this purpose, at the insertion position (supply position), the bottle mouth of the tilted sample bottle 111 opposes an upper portion of the taper portion 151, and the cylinder 41 of the plastometer 1 opposes the lower end of the straight pipe portion 152. Reference numeral 142 in the drawings denotes a vibrator. The vibrator 142 vibrates the hopper 117 so that the sample Sa passing through the hopper 117 does not adhere to the inner surface of the hopper 117.

Figure 15:
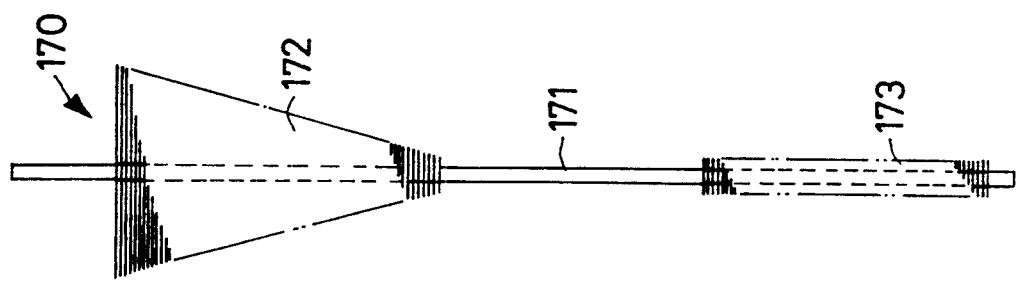
FIG. 15 is a side view of a brush body.
Figure 14:
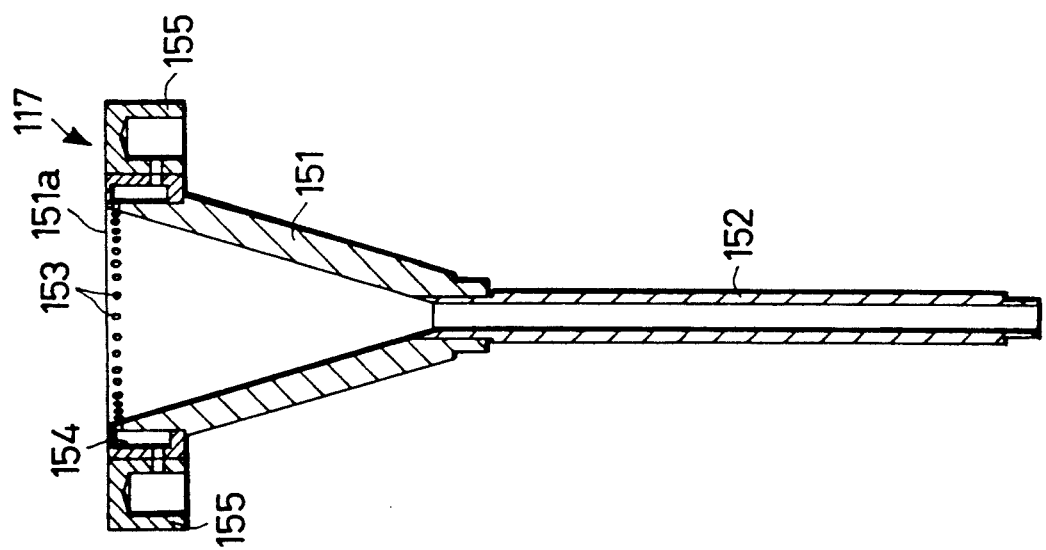
FIG. 14 is a sectional view of the hopper.

As shown in FIG. 14, a plurality of suction openings 153 are formed in an upper end portion 151a of the taper portion 151 of the hopper 117 in the circumferential direction, and a suction chamber 154 is mounted to externally surround the upper end portion 151a from outside the hopper 117. The suction openings 153 communicate with the suction chamber 154, and the suction chamber 154 (see FIG. 15) communicates with a vacuum pump 56 through connection ports 155 of two opposing vacuum hoses (not shown). The hopper unit is constituted in this manner. The residual sample Sa adhering to the inner surface of the hopper 117 is drawn by vacuum during cleaning of the hopper 117 (to be described later), and the sample (mainly the powder type sample) Sa which is blown up while it is filled in the hopper 117 is drawn by vacuum to prevent it from scattering to the outside. The sample Sa filled in the cylinder 41 is heated to melt. At this time, the sample Sa is sufficiently rammed by the rammer 118 so that bubbles will not be formed during heating and melting.

The rammer 118 is arranged on the same axis as that of the hopper 117 at the insertion position (supply position) and is fixed to the side wall 2a of the machine table 2 through a rodless cylinder 157. The rodless cylinder 157 comprises a cylinder body 118 and a rail section 159, and is driven by the cylinder body 158 to vertically move along the rail section 159. An upper end of the rammer 118 is fixed to the cylinder body 158. When the cylinder body 158 is driven, the rammer 118 is inserted in the cylinder 41 of the plastometer 1 by using the hopper 117 as a guide, and rams the sample Sa.

As described above, the sample bottle 111 is tilted by the sample bottle tilter 113 while it is rotated by the sample bottle rotator 115, and its interior is relatively agitated by the agitator 116. Therefore, the sample Sa is easily removed from the inner circumferential surface of the sample bottle 111 and pours out into the hopper 117. The plastic sample Sa which has poured out does not easily attach to the inner surface of the hopper 117 and is directly guided into the cylinder 41 of the plastometer 1, as the lower portion of the hopper 117 forms the straight pipe portion 152 and the hopper 117 is vibrated by the vibrator 59. As a result, the sample Sa does not remain in the sample bottle 111 or clog in the hopper 117, and the sample Sa is supplied into the cylinder 41 smoothly and reliably.

The cleaning unit 26 will be described in detail with reference to FIGS. 10, 12, 15, and 16.

The cleaning unit 26 is effective in handling mainly a powder type sample Sa. The cleaning unit 26 cleans the rammer 118 and the hopper 117 that directly contact the sample Sa, thereby preventing the residual sample Sa from being mixed in a sample Sa for a subsequent test to denature it. The cleaning unit 26 comprises a rammer cleaner 161 for cleaning the rammer 118, and an internal hopper cleaner 162 and a lower end hopper cleaner 163 both for cleaning the hopper 117.

The rammer cleaner 161 is fixed to the side wall 2a of the machine table 2 at a lower portion of the rodless cylinder 157. The rammer 118 is inserted in the central portion of the rammer cleaner 161, and the rammer cleaner 161 also serves as a guide for vertically moving of the rammer 118. A contact member 165 is stored in a case 164 of the rammer cleaner 161 to surround the inserted rammer 118. When driven by the rodless cylinder 157, the rammer 118 slidably contacts the contact member 165. The contact member 165 and the rodless cylinder 157 constitute a scraping means for the residual sample Sa. A connection port 166 communicating with the vacuum pump 156 (see FIG. 16) to draw by vacuum the residual sample Sa scraped by the contact member 165 is formed in the front surface of the case 164. The case 164, the connection port 166, the vacuum hoses (not shown), and the vacuum pump 156 constitute the rammer suction cleaning means. The rammer 118 is vertically moved by the rodless cylinder 157, and the residual sample Sa adhering to the surface of the rammer 118 is scraped by the contact member 165. The vacuum pump 156 performs vacuum suction in an interlocked manner with this vertical movement, and the residual sample Sa scraped off into the case 164 is drawn by vacuum and removed from the interior of the case 164.

In the internal hopper cleaner 162, a motor 168 is mounted on an actuator 167 fixed to the side wall 2a of the machine table 2, and a brush body 170 consisting of a rod 171 and first and second brushes 172 and 173 is mounted on a rotating shaft 169 of the motor 168, thereby constituting the brush means. As shown in FIG. 14, the first brush 172 has an inverted conical shape to match the shape of the inner surface of the taper portion 151 of the hopper 117. The second brush 173 has a columnar shape to match the shape of the inner surface of the straight pipe portion 152 of the hopper 117. Both the first and second brushes 172 and 173 stand upright on the rod 171. After a sample supply, the hopper 117 is moved to the cleaning position by the horizontal/vertical movable rail, and is aligned on the same axis as that of the rotating shaft 169 of the motor 168. The brush body 170 is moved downward by drive of the actuator 167 while it is rotated by drive of the motor 168, and is inserted in the hopper 117 from above.

Regarding the residual sample Sa adhering to the inner surface of the hopper 117, that partion adhering to the taper portion 151 is scraped by the first brush 172, and that partion adhering to the straight pipe portion 152 is scraped by the second brush 173, thus performing cleaning.

Regarding the scraped residual sample Sa, at an upper portion of the hopper 117, it is drawn by vacuum through the above-described suction openings 153 of the hopper 117 and processed, and at a lower portion of the hopper 117, it is drawn by vacuum by the lower end hopper cleaner 163 through the lower end of the hopper 117 and processed.

The lower end hopper cleaner 163 comprises a main body 174, a cleaning head 175, a drive motor 176, and an elevating cylinder 177, and is fixed to the machine table 2 through the elevating cylinder 177. The cleaning head 175 is rotatably mounted on the main body 174 and is connected to the lower end of the hopper 117 in an abutting manner. The drive motor 176 is incorporated in the main body 174 and rotates the cleaning head 175. The elevating cylinder 177 vertically moves the main body 174. The cleaning head 175 is positioned on the same axis as that of the hopper 117 at the cleaning position and incorporates a rotary brush and a suction port (neither are shown). The residual sample Sa in the hopper 117 is drawn by vacuum through the suction port and is guided to the vacuum pump 156, and the rotary brush scrapes the molten sample Sa which adhered during sample supply. The cleaning head 175 is rotated by the drive motor 176 through a belt 178, and is vertically moved by the elevating cylinder 177 together with the main body 174 to oppose the lower end of the hopper 117 at the cleaning position. In this manner, the lower end hopper cleaner 163 constitutes the hopper suction cleaning means together with the vacuum pump 156 and the vacuum hoses (not shown), and is connected to the lower end of the hopper 117 to draw by vacuum the residual sample Sa scraped by the internal hopper cleaner 162.

Simultaneously, the residual sample Sa at the lower end of the hopper 117 is scraped by the rotary brush of the cleaning head 175 and is drawn by vacuum by the internal hopper cleaner 162.

Peripheral members of the vacuum pump are, as shown in FIG. 16, a filter 179 and a selector valve 180 at an upstream side of the vacuum pump 156. Vacuum suction of the respective constituent units is selectively performed by the selector valve 180, and the residual sample Sa subjected to vacuum suction is collected and removed by the filter 179.

The operating steps of the cleaning unit 26 will be briefly described.

When ramming of the sample Sa filled in the cylinder 41 by the rammer 118 is completed, the rammer 118 is moved upward to remove the residual sample Sa adhering to the rammer 118 by the rammer cleaner 161. When the rammer 118 is removed from the cylinder 41 and the hopper 117 and stopped, the hopper 117 is slightly moved upward so that its lower end is extracted from the cylinder 41. Subsequently, the rammer 118 is vertically moved again to be inserted in the hopper 117. During this reciprocal movement, the residual sample Sa adhering to the rammer 118 is removed by the rammer cleaner 161. Then, the hopper 117 is moved to the cleaning position. After this movement, the rammer 118 is vertically moved again, thus completing cleaning of the rammer 118. Meanwhile, the cleaning head 175 of the lower end hopper cleaner 163 is moved upward from below toward the hopper 117 moved to the cleaning position, is connected to it, and starts cleaning drive.

Simultaneously, the rotating brush body 170 of the internal hopper cleaner 162 is moved downward from an upper portion of the hopper 117, and is inserted in the hopper 117. When insertion of the brush body 170 is completed, only its downward movement is stopped, and cleaning of the residual sample Sa by the rotation of the brush body 170 is performed during a predetermined period of time. After that, the brush body 170 is moved upward and its rotation is stopped, and subsequently the cleaning head 175 of the lower end hopper cleaner 163 is moved downward. Cleaning is completed, and the hopper 117 is moved to the sample supply position.

As described above, according to this embodiment, the rammer 118 is brought into a slidable contact with the contact member 165 of the rammer cleaner 161. Therefore, the residual sample Sa can be automatically scraped by utilizing the vertical movement of the rammer 118. Also, the scraped residual sample Sa is automatically drawn by vacuum so that it will not scatter to the outside to cause contamination. In addition, the contact member 165 can be utilized as a guide for vertical movement of the rammer 118. The residual sample Sa on the inner surface of the hopper 117 is automatically scraped by drive of the brush body 170 of the internal hopper cleaner 162, and is automatically drawn by vacuum by the lower end hopper cleaner 163. Therefore, the sample Sa is reliably removed without scattering to the outside.

In this case, since the brush body 170 is constituted by the first and second brushes 172 and 173 and is rotated and vertically moved, the residual sample Sa can be scraped in a manner to match the shape of the inner surface of the hopper, and the residual sample Sa can be reliably removed.

Since the rotary brush is incorporated in the cleaner head 175 of the lower end hopper cleaner 163, the lower end of the hopper 117 to which the molten sample can easily adhere can be reliably cleaned.

Because of the presence of the suction openings 53 of the hopper 117, the residual sample Sa scraped during cleaning will not scatter to the outside, and the sample Sa will not scatter to the outside during supply even if it is a powder type sample Sa, thereby preventing contamination by the sample Sa.

As described above, since the strand bottle, the strand bottle stocker, the weight measuring unit, the strand cutting unit, and the strand bottle convey unit are provided, a series of operations including strand cutting, weight measurement, and strand bottle stocking can be automatically performed. Especially, if a convey robot is used, transfer of the strand bottle can be automated smoothly and assuredly.

Since the strand bottle having the cutting edge, and the fixing means, the elevating means, and the reciprocating means for the strand bottle are provided, the cutting operation is performed automatically.

Simultaneously, the cut strand can be automatically caught, thereby performing cutting and catching operations of the strand very efficiently.

In this case, if the strand bottle can be detached from the fixing means, the cut strand can be weighed and stocked as it is stored in the strand bottle, thereby performing these operations efficiently.

If the fixing means is constituted by the first fixing means for guiding insertion of the strand bottle and for fixing the travel direction and the second fixing means for fixing the vertical direction, only the strand bottle can be vertically moved by using the first fixing means as a guide, and the first fixing means can be utilized to receive the reaction force which occurs during cutting, making the overall structure without any loss.

In this case, if the first fixing means can regulate the movement of the strand bottle in the horizontal rotating direction, the direction of the cutting edge of the strand bottle can be regulated, and the direction of the cutting edge can be easily directed in a desired direction only by fixing the strand bottle. Since the second fixing means has the chucking port for chucking the strand bottle and the chucking port is constituted by an elastic member, the chucking operation of the strand bottle is performed easily, and the cutting edge can be biased toward the die, thus cutting the strand reliably.

According to this invention, three strand bottles can be caused by the control means to catch the strand continuously. Thus, three test operations required by the JIS can be performed quite reliably without any loss.

In this case, if the control means stops the strand bottle immediately after cutting and moves the strand bottle downward, the cut strand will not partly adhere to the die, thus preventing defective cutting of the strand.

If the base has the cutting mechanism for cutting the preheated strand, so-called waste cutting can be automatically performed by using the strand cutting unit, and the timing of test start can be set by the waste cutting.

In this case, if the cutting mechanism has the moving means for moving the cutting edge between the cutting position and the escape position, the cutting edge can be caused to function effectively only for waste cutting. If the cutting edge is mounted through one point to be capable of being inclined in the direction of the edge trace with respect to the moving means, the edge trace of the cutting edge constantly maintains the abutting state against the die during cutting, and waste cutting of the strand is reliably performed.

If the cutting mechanism is a strand bottle having the cutting edge, the strand subjected to waste cutting can be automatically collected in the strand bottle.

According to this invention, the cutting edge is fixed to the bottle body with its tip located immediately above the bottle mouth. Therefore, catching of the cut strand can be reliably performed automatically regardless of the viscosity of the strand. As a result, the cutting speed can be decreased.

In this case, if the edge trace of the cutting edge is substantially perpendicular to the cutting direction, even a strand having a high viscosity can be reliably cut. Also, since the cutting edge is formed in a V-shape manner, the strand after cutting will not easily adhere to the cutting edge, and the cutting edge need not be cleaned even when the strand bottle is used repeatedly.

If the bottle body is formed as a polygonal prism, the cutting edge can be better mounted and the bottle body can be better held by the robot. If the bottle mouth of the bottle body is set to be larger than the distance of the cutting movement, the strand can be caught more reliably.

According to this invention, since the cutting edge is fixed to the bottle body, cutting and catching of the strand can be performed efficiently.

If three strands bottles of this type are prepared, three test operations required by the JIS can be performed reliably within a short period of time.

According to this invention, since the sample container is tilted while it is rotated by the tilting means and the rotating means, the plastic sample can be easily removed from the inner circumferential surface of the sample container. Therefore, the sample is prevented from remaining in the sample container, and can be reliably supplied into the cylinder.

In addition, if the plastic sample in the sample container is agitated by the agitating means, it reliably pours out even if it is a sample having a high adhesion strength. Therefore, the sample can be supplied more reliably.

If the vibrating means for vibrating the hopper is provided, adhesion of the plastic sample to the inner surface of the hopper is suppressed. Therefore, smooth sample supply into the cylinder is enabled.

If the lower portion of the hopper forms a straight pipe portion, the sample is prevented from clogging in the hopper, and smooth, reliable sample supply into the cylinder is enabled.

Thus, the present invention has an effect to be able to efficiently perform tests of various types of samples including a powder type sample or an adherent sample.

In addition, according to this invention, since the brush means for scraping the residual sample adhering to the hopper and the hopper suction cleaning means for drawing by vacuum the residual sample are provided, automatic cleaning of the hopper is enabled. Also, since the scraping means for scraping the residual sample adhering to the rammer and the rammer suction cleaning means for drawing by vacuum the residual sample are provided, automatic cleaning by the rammer is enabled. Furthermore, since these cleaning operations can be performed simultaneously, the cleaning time is shortened, and the overall test time can be shortened. Also, since the residual sample is drawn by vacuum, contamination by the sample is prevented.

In this case, if the brush means has a brush body of a shape matching the shape of the inner surface of the hopper, cleaning that matches the shape of the inner surface of the hopper is enabled. Also, if the brush means is rotated with respect to the hopper and is inserted in or removed from the hopper, the residual sample can be reliably removed.

If the rotary brush is incorporated in the hopper suction cleaning means, the residual sample at the lower end of the hopper to which the molten sample can easily adhere can be reliably removed.

If the scraping means and the rammer suction cleaning means are provided on the same axis as that of the hopper located at the sample supply position, some constituent components of the rammer suction cleaning means can be partly omitted, thus decreasing the number of components.

Since the suction openings and the suction means for the hopper are provided, the sample can be prevented from scattering not only during cleaning but also during sample supply, thereby preventing contamination by the sample.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

We claim:

1. A flow tester for a thermoplastic which uses an extrusion type plastometer comprising a vertically supported cylinder, a piston on which a weight is mounted at an upper portion thereof and which is inserted in said cylinder, a die mounted on a lower end of said cylinder, and a heater provided to surround said cylinder, wherein a sample of a thermoplastic is filled in said cylinder and is heated by said heater to melt, the molten sample is extruded from said die by said piston, a strand as an extruded material is cut, and a mass thereof is obtained, thereby testing a flow characteristic of the thermoplastic, characterized by:

a strand bottle which has a cutting edge for cutting the strand and which catches the strand cut by said cutting edge;

a strand bottle stocker for storing said strand bottle before and after use;

a weight measuring unit for measuring a weight of the cut strand together with said strand bottle, a strand cutting unit for moving said strand bottle so that said cutting edge of said strand bottle travels along a lower end face of said die to perform cutting, and a strand bottle convey unit for transferring and conveying said strand bottle among said strand bottle stocker, said weight measuring unit, and said strand cutting unit.

2. The flow tester for a thermoplastic according to claim 1, wherein said strand bottle convey unit has a convey robot for holding and conveying said strand bottle.

3. A flow tester for a thermoplastic, providing a strand cutting unit, said flow tester using an extrusion type plastometer comprising a vertically supported cylinder, a piston on which a weight is mounted to an upper portion thereof and which is inserted in said cylinder, a die mounted at a lower end of said cylinder and a heater provided to surround said cylinder, wherein a sample of a thermoplastic is filled in said cylinder and is heated by said heater to melt, the molten sample is extruded from said die by said piston, a strand as an extruded material is cut and a mass thereof is obtained, thereby testing a flow characteristic of the thermoplastic, characterized in said strand cutting unit comprising:

a strand bottle which has a cutting edge for cutting the strand and which catches the strand cut by said cutting edge;

fixing means for placing and fixing said strand bottle on a base;

elevating means for vertically moving said strand bottle through said fixing means so as to move said cutting edge of said strand bottle between an abutting position to abut against a lower end face of said die and a separate position as a position before and after a cutting operation; and reciprocating means for reciprocating said strand bottle through said fixing means so as to cause said cutting edge to travel between a cutting start position and a cutting end position by sandwiching said die in between.

4. The flow tester for a thermoplastic according to claim 3, wherein said fixing means is constituted to be capable of detaching said strand bottle from said base.

5. The flow tester for a thermoplastic according to claim 3, wherein said fixing means comprises:

first fixing means for guiding insertion of said strand bottle in the vertical direction and for fixing a movement of said cutting edge in a travel direction, and second fixing means for fixing a movement of said strand bottle in the vertical direction.

6. The flow tester for a thermoplastic according to claim 5, wherein said first fixing means and said strand bottle have a recess and a projection that engage with each other to fix a movement of said strand bottle in a horizontal rotating direction.

7. The flow tester for a thermoplastic according to claim 5, wherein said second fixing means has a chucking port for chucking a lower surface of said strand bottle.

8. The flow tester for a thermoplastic according to claim 7, wherein said chucking port is constituted by an elastic member.

9. The flow tester for a thermoplastic according to claim 3, wherein said strand cutting unit is capable of loading three strand bottles thereon; and said strand cutting unit further comprises control means for controlling cutting travel of said strand bottles at desired time intervals.

10. The flow tester for a thermoplastic according to claim 9, wherein said control means comprises a control section for controlling said reciprocating means to stop cutting travel of said strand bottle immediately after strand cutting and to move said strand bottle downward immediately after the cutting travel is stopped.

11. The flow tester for a thermoplastic according to claim 3, wherein said strand cutting unit further comprises a cutting mechanism, mounted on said base ahead of a cutting direction of said strand bottle, for cutting a preheated strand portion as a test start.

12. The flow tester for a thermoplastic according to claim 11, wherein said cutting mechanism comprises:

a cutting member for cutting the strand, and moving means for moving said cutting member between a cutting position where said cutting member abuts against the lower end face of said die and the escape position as the position before and after the cutting operation.

13. The flow tester for a thermoplastic according to claim 12, wherein said cutting member is a cutting edge, and supported at a point to be capable of being inclined in an edge trace direction with respect to said moving means.

14. The flow tester for a thermoplastic according to claim 12, wherein said cutting member is a strand bottle comprising a cutting edge and a bottle body for catching the strand cut by said cutting edge.

15. A flow tester for a thermoplastic providing a strand bottle, said flow tester using an extrusion type plastometer comprising a vertically supported cylinder, a piston on which a weight is mounted at an upper portion thereof and which is inserted in said cylinder, a die mounted on a lower end of said cylinder, and a heater provided to surround said cylinder, wherein a sample of a thermoplastic is filled in said cylinder and is heated by said heater to melt, the molten sample is extruded from said die by said piston, a strand as an extruded material is cut, and a mass thereof is obtained, thereby testing a flow characteristic of the thermoplastic, characterized in that said strand bottle comprises:

a bottle body for catching the cut strand, and a cutting edge for strand cutting, said cutting edge being fixed to said bottle body while a tip thereof is located immediately above a bottle mouth of said bottle body.

16. The flow tester for a thermoplastic according to claim 15, wherein said cutting edge is fixed to said bottle body such that an edge trace thereof is aligned in a direction substantially perpendicular to a cutting direction within a horizontal plane.

17. The flow tester for a thermoplastic according to claim 15, wherein said tip of said cutting edge is formed to have a V-shaped section slightly inclined in a cutting direction.

18. The flow tester for a thermoplastic according to claim 15, wherein said bottle body is formed to have an outer shape of a polygonal prism.

19. The flow tester for a thermoplastic according to claim 15, wherein a width of said bottle mouth of said bottle body in a cutting direction is larger than a travel distance for strand cutting.

20. A strand cutting method of a flow tester for a thermoplastic, said flow tester using an extrusion type plastometer comprising a vertically supported cylinder, a piston on which a weight is mounted at an upper portion thereof and which is inserted in said cylinder, a die mounted on a lower end of said cylinder, and a heater provided to surround said cylinder, wherein a sample of a thermoplastic is filled in said cylinder and is heated by said heater to melt, the molten sample is extruded from said die by said piston, a strand as an extruded material is cut, and a mass thereof is obtained, thereby testing a flow characteristic of the thermoplastic, characterized by:

using a strand bottle comprising a cutting edge for strand cutting and a bottle body for catching the strand cut by said cutting edge, and moving said strand bottle such that said cutting edge thereof travels along a lower end face of said die, thereby cutting the strand.

21. The strand cutting method according to claim 20, characterized in that:

three strand bottles are used, and cutting of the strand by said strand bottles is sequentially performed at desired time intervals.

* * * * *